US010464977B2

(12) United States Patent
Jabra-Rizk et al.

(10) Patent No.: US 10,464,977 B2
(45) Date of Patent: Nov. 5, 2019

(54) HISTATIN-5 BASED SYNTHETIC PEPTIDES AND USES THEREOF

(71) Applicants: Mary Ann Jabra-Rizk, Timonium, MD (US); Amy J. Karlsson, Silver Spring, MD (US); Svetlana Pavlova Ikonomova, Silver Spring, MD (US)

(72) Inventors: Mary Ann Jabra-Rizk, Timonium, MD (US); Amy J. Karlsson, Silver Spring, MD (US); Svetlana Pavlova Ikonomova, Silver Spring, MD (US)

(73) Assignees: University of Maryland, Baltimore, Baltimore, MD (US); University of Maryland, College Park, College Park, MD (US)

( * ) Notice: Subject to any disclaimer, the term of this patent is extended or adjusted under 35 U.S.C. 154(b) by 0 days.

(21) Appl. No.: 15/484,463

(22) Filed: Apr. 11, 2017

(65) Prior Publication Data

US 2017/0291930 A1    Oct. 12, 2017

Related U.S. Application Data

(60) Provisional application No. 62/480,054, filed on Mar. 31, 2017, provisional application No. 62/320,675, filed on Apr. 11, 2016.

(51) Int. Cl.
| | |
|---|---|
| *A61K 38/00* | (2006.01) |
| *C07K 14/47* | (2006.01) |
| *A61L 26/00* | (2006.01) |
| *A61L 15/32* | (2006.01) |
| *A61L 15/44* | (2006.01) |
| *A61L 15/60* | (2006.01) |

(52) U.S. Cl.
CPC .......... *C07K 14/4723* (2013.01); *A61L 15/32* (2013.01); *A61L 15/44* (2013.01); *A61L 15/60* (2013.01); *A61L 26/008* (2013.01); *A61L 26/0047* (2013.01); *A61L 26/0066* (2013.01); *A61K 38/00* (2013.01); *A61L 2300/252* (2013.01); *A61L 2300/404* (2013.01)

(58) Field of Classification Search
None
See application file for complete search history.

(56) References Cited

U.S. PATENT DOCUMENTS 6,126,939 A * 10/2000 Eisenbach-Schwartz ...................
C07K 5/06095
424/185.1
7,005,500 B2 * 2/2006 Bejanin .................. C07K 14/47
530/350

OTHER PUBLICATIONS

NCBI Reference Sequence NP002150.1 (downloaded on Mar. 26, 2018 from URL:<https://www.ncbi.nlm.nih.gov/protein/NP_002150>) (Year: 2018).*
Brigham et al. (Tissue Eng Part A. Jul. 2009;15(7):1645-53) (Year: 2009).*
Tati et al. (Antimicrob Agents Chemother. 2014;58(2):756-66) (Year: 2014).*
Nordone et al. (Aids Research and Human Retroviruses, vol. 22, No. 6, 2006, pp. 558-568) (Year: 2006).*
GenBank AAD01397.1 (downloaded on Mar. 26, 2018 from URL: <https://www.ncbi.nlm.nih.gov/protein/AAD01397.1>) (Year: 2018).*
Kadowaki et al. (Mol Pharmacol. Dec. 2004;66(6):1599-606) (Year: 2004).*
Storz et al. (Intellectual Property Issues: Therapeutics, Vaccines and Molecular Diagnostics, Springer Science & Business Media, May 11, 2012) (Year: 2012).*
Hipkiss et al. (Ann N Y Acad Sci. Nov. 20, 1998;854:37-53) (Year: 1998).*
Fuhrmann et al. (Journal of Controlled Release 205 (2015) 35-44) (Year: 2015).*
Kong et al. (Antimicrob Agents Chemother. Nov. 23, 2015;60(2):881-9) (Year: 2015).*
Rawlings, N. D., Barrett, A. J., and Bateman, A. (2012) MEROPS: the database of proteolytic enzymes, their substrates and inhibitors, Nucleic Acids Res. 40, D343-D350.
Albrecht, A., Felk, A., Pichova, I., Naglik, J. R., Schaller, M., de Groot, P., Maccallum, D., Odds, F. C., Schafer, W., Klis, F., Monod, M., and Hube, B. (2006) Glycosylphosphatidylinositol-anchored proteases of Candida albicans target proteins necessary for both cellular processes and host-pathogen interactions, J. Biol. Chem. 281, 688-694.
Naglik, J. R., Challacombe, S. J., and Hube, B. (2003) Candida albicans secreted aspartyl proteinases in virulence and pathogenesis, Microbiol. Mol. Biol. Rev. 67, 400-428.
Naglik, J. R., Moyes, D., Makwana, J., Kanzaria, P., Tsichlaki, E., Weindl, G., Tappuni, A. R., Rodgers, C. A., Woodman, A. J., Challacombe, S. J., Schaller, M., and Hube, B. (2008) Quantitative expression of the Candida albicans secreted aspartyl proteinase gene family in human oral and vaginal candidiasis, Microbiology 154, 3266-3280.
Rapala-Kozik, M., Bochenska, O., Zawrotniak, M., Wolak, N., Trebacz, G., Gogol, M., Ostrowska, D., Aoki, W., Ueda, M., and Kozik, A. (2015) Inactivation of the antifungal and immunomodulatory properties of human cathelicidin LL-37 by aspartic proteases produced by the pathogenic yeast Candida albicans, Infect. Immun. 83, 2518-2530.

(Continued)

*Primary Examiner* — Sergio Coffa
(74) *Attorney, Agent, or Firm* — Benjamin Aaron Adler

(57) ABSTRACT

Provided herein are synthetic peptides or synthetic fragments thereof based on a Histatin-5 peptide, for example with a sequence DSHAKRHHGYKRKFHEKHHSHRGY (SEQ ID NO: 1). The synthetic peptides or synthetic fragments have at least one substituted amino acid that is arginine and/or leucine to increase resistance to proteolytic degradation by a microbe, such as a fungus. The synthetic peptides or synthetic fragments thereof may be contained in a hydrogel. Also provided are methods for treating or preventing a pathophysiological condition via topical administration of the synthetic peptide or fragments. The pathophysiological condition may be a fungal or bacterial infection including associated inflammation or a chronic condition.

10 Claims, 17 Drawing Sheets

Specification includes a Sequence Listing.

(56) References Cited

OTHER PUBLICATIONS

Meiller, T. F., Hube, B., Schild, L, Shirtliff, M. E., Scheper, M. A., Winkler, R., Ton, A., and Jabra-Rizk, M. A. (2009) A novel immune evasion strategy of Candida albicans: proteolytic cleavage of a salivary antimicrobial peptide, PLoS One 4, e5039.
Bochenska, O., Rapala-Kozik, M., Wolak, N., Aoki, W., Ueda, M., and Kozik, A. (2016) The action of ten secreted aspartic proteases of pathogenic yeast Candida albicans on major human salivary antimicrobial peptide, histatin 5, Acta Biochim. Pol. 63, 403-410.
Oppenheim, F. G., Xu, T., McMillian, F. M., Levitz, S. M., Diamond, R. D., Offner, G. D., and Troxler, R. F. (1988) Histatins, a novel family of histidine-rich proteins in human parotid secretion. Isolation, characterization, primary structure, and fungistatic effects on Candida albicans, J. Biol. Chem. 263, 7472-7477.
Xu, T., Levitz, S. M., Diamond, R. D., and Oppenheim, F. G. (1991) Anticandidal activity of major human salivary histatins, Infect. Immun. 59, 2549-2554.
Khan, S. A., Fidel, P. L., Thunayyan, A. A., Varlotta, S., Meiller, T. F., and Jabra-Rizk, M. A. (2013) Impaired Histatin-5 Levels and Salivary Antimicrobial Activity against C. albicans in HIV Infected Individuals, Journal of AIDS & clinical research 4, 193.
Helmerhorst, E J., van't Hof, W., Breeuwer, P., Veerman, E. C. I., Abee, T., Troxler, R. F., Amerongen, A. V. N., and Oppenheim, F. G. (2001) Characterization of histatin 5 with respect to amphipathicity, hydrophobicity, and effects on cell and mitochondrial membrane integrity excludes a candidacidal mechanism of pore formation, J. Biol. Chem. 276, 5643-5649.
Puri, S., and Edgerton, M. (2014) How does it kill?: understanding the candidacidal mechanism of salivary histatin 5, Eukaryot. Cell 13, 958-964.
Xu, J., and Mitchell, T. G. (2003) Geographical differences in human oral yeast flora, Clin. Infect. Dis. 36, 221-224.
Schild, L., Heyken, A., de Groot, P. W., Hiller, E., Mock, M., de Koster, C., Horn, U., Rupp, S., and Hube, B. (2011) Proteolytic cleavage of covalently linked cell wall proteins by Candida albicans Sap9 and Sap10, Eukaryot. Cell 10, 98-109.
Tsai, H., Raj, P. A., and Bobek, L. A. (1996) Candidacidal activity of recombinant human salivary histatin-5 and variants, Infect. Immun. 64, 5000-5007.
Rothstein, D. M., Spacciapoli, P., Tran, L. T., Xu, T., Roberts, F. D., Dalla Serra, M., Buxton, D. K., Oppenheim, F. G., and Friden, P. (2001) Anticandida activity is retained in P-113, a 12-amino-acid fragment of histatin 5, Antimicrob. Agents Chemother. 45, 1367-1373.
Ruissen, A. L., Groenink, J., Helmerhorst, E. J., Walgreen-Weterings, E., Van't Hof, W., Veerman, E. C., and Nieuw Amerongen, A. V. (2001) Effects of histatin 5 and derived peptides on Candida albicans, Biochem. J. 356, 361-368.
Matejuk, A., Leng, Q., Begum, M. D., Woodle, M. C., Scaria, P., Chou, S. T., and Mixson, A. J. (2010) Peptide-based antifungal therapies against emerging infections, Drugs Future 35, 197.
Jang, W. S., Li, X. S., Sun, J. N., and Edgerton, M. (2008) The P-113 fragment of histatin 5 requires a specific peptide sequence for intracellular translocation in Candida albicans, which is independent of cell wall binding, Antimicrob. Agents Chemother. 52, 497-504.
Helmerhorst, E. J., Van't Hof, W., Veerman, E. C., Simoons-Smit, I., and Nieuw Amerongen, A. V. (1997) Synthetic histatin analogues with broad-spectrum antimicrobial activity, Biochem. J. 326 ( Pt 1), 39-45.
Helmerhorst, E. J., Reijnders, I. M., van 't Hof, W., Veerman, E. C., and Nieuw Amerongen, A. V. (1999) A critical comparison of the hemolytic and fungicidal activities of cationic antimicrobial peptides, FEBS Lett. 449, 105-110.
Li, X. S., Reddy, M. S., Baev, D., and Edgerton, M. (2003) Candida albicans Ssa1/2p is the cell envelope binding protein for human salivary histatin 5, J. Biol. Chem. 278, 28553-28561.
Borg-von Zepelin, M., Beggah, S., Boggian, K., Sanglard, D., and Monod, M. (1998) The expression of the secreted aspartyl proteinases Sap4 to Sap6 from Candida albicans in murine macrophages, Mol. Microbiol. 28, 543-554.
Dash, C., Kulkami, A., Dunn, B., Rao, M. (2003) Aspartic peptidase inhibitors: implications in drug development, Crit. Rev. Biochem. Mol. Biol. 38, 89-119.
Monod, M., Capocciaa, S., Lechennea, B., Zaugga, C., Holdomb, M., Joussona, O. (2002) Secreted proteases from pathogenic fungi, Int. J. Med. Microbiol. 292, 405-419.
Bochenska, O., Rapala-Kozik, M., Wolak, N., Kamysz, W., Grzywacz, D., Aoki, W., Ueda, M., Kozik, A. (2015) Inactivation of human kininogen-derived antimicrobial peptides by secreted aspartic proteases produced by the pathogenic yeast *Candida albicans*, Biol. Chem. 396, 1369-1375.
Aoki, W., Kitahara, N., Miura, N., Morisaka, H., Yamamoto, Y., Kuroda, K., Ueda, M. (2011) Comprehensive characterization of secreted aspartic proteases encoded by a virulence gene family in *Candida albicans*, J Biochem 150, 431-438.
Koelsch, G., Tang, J., Loy, J.A., Monod, M., Jackson, K, Foundling, S.I., Lin, X. (2000) Enzymic characteristics of secreted aspartic proteases of Candida albicans, Biochim. Biophys. Acta 1480, 117-131.
Laskay, Ü. A., Srzentića, K., Monod, M., Tsybina, Y.O. (2014) Extended bottom-up proteomics with secreted aspartic protease Sap9, Journal of Proteomics 110, 20-31.
Driscoll, J., Duan, C., Zuo, Y., Xu, T., Troxler, R., Oppenheim, F.G. (1996) Candidacidal activity of human salivary histatin recombinant variants produced by site-directed mutagenesis, Gene 177, 29-34.
Situ, H., Balasubramanian, S.V., Bobek, L.A. (2000) Role of α-helical conformation of histatin-5 in candidacidal activity examined by proline variants, Biochimica et Biophysica Acta (BBA)— General Subjects 1475, 377-382.
Karlsson, A. J., Pomerantz, W.C., Neilsen, K.J., Gellman, S.H., Palecek, S.P. (2009) Effect of sequence and structural properties on 14-helical b-peptide activity against Candida albicans planktonic cells and biofilms, ACS Chem. Biol. 4, 567-579.
Ruissen, A. L., Groenink, J., Krijtenberg, P., Walgreen-Weterings, E., van't Hof, W., Veerman, E.C.I., Amerongen, A.V.N. (2003) Internalisation and degradation of histatin 5 by Candida albicans, Biol. Chem. 384, 183-190.

\* cited by examiner

SEQUENCE LISTING

<160> NUMBER OF SEQ ID NOS: 14

<210> SEQ ID NO 1
<211> LENGTH: 24
<212> TYPE: PRT
<213> ORGANISM: Artificial sequence
<220> FEATURE:
<223> OTHER INFORMATION: Sequence of Histatin-5 peptide

<400> SEQUENCE: 1

Asp Ser His Ala Lys Arg His His Gly Tyr Lys Arg Lys Phe His Glu
1               5                   10                  15

Lys His His Ser His Arg Gly Tyr
            20

<210> SEQ ID NO 2
<211> LENGTH: 24
<212> TYPE: PRT
<213> ORGANISM: Artificial sequence
<220> FEATURE:
<222> LOCATION: 5
<223> OTHER INFORMATION: Sequence of Histatin-5 peptide substituted with
      an Arg at position 5

<400> SEQUENCE: 2

Asp Ser His Ala Arg Arg His His Gly Tyr Lys Arg Lys Phe His Glu
1               5                   10                  15

Lys His His Ser His Arg Gly Tyr
            20

<210> SEQ ID NO 3
<211> LENGTH: 24
<212> TYPE: PRT
<213> ORGANISM: Artificial sequence
<220> FEATURE:
<222> LOCATION: 5
<223> OTHER INFORMATION: Sequence of Histatin-5 peptide substituted with
      a Leu at position 5

<400> SEQUENCE: 3

Asp Ser His Ala Leu Arg His His Gly Tyr Lys Arg Lys Phe His Glu
1               5                   10                  15

Lys His His Ser His Arg Gly Tyr
            20

<210> SEQ ID NO 4
<211> LENGTH: 24
<212> TYPE: PRT
<213> ORGANISM: Artificial sequence
<220> FEATURE:
<222> LOCATION: 11
<223> OTHER INFORMATION: Sequence of Histatin-5 peptide substituted with
      an Arg at position 11

<400> SEQUENCE: 4

Asp Ser His Ala Lys Arg His His Gly Tyr Arg Arg Lys Phe His Glu
1               5                   10                  15

Lys His His Ser His Arg Gly Tyr
            20

<210> SEQ ID NO 5
<211> LENGTH: 24
<212> TYPE: PRT
<213> ORGANISM: Artificial sequence
<220> FEATURE:
<222> LOCATION: 11

```
<223> OTHER INFORMATION: Sequence of Histatin-5 peptide substituted with
      a Leu at position 11

<400> SEQUENCE: 5

Asp Ser His Ala Lys Arg His His Gly Tyr Leu Arg Lys Phe His Glu
1               5                   10                  15

Lys His His Ser His Arg Gly Tyr
            20

<210> SEQ ID NO 6
<211> LENGTH: 24
<212> TYPE: PRT
<213> ORGANISM: Artificial sequence
<220> FEATURE:
<222> LOCATION: 13
<223> OTHER INFORMATION: Sequence of Histatin-5 peptide substituted with
      an Arg at position 13

<400> SEQUENCE: 6

Asp Ser His Ala Lys Arg His His Gly Tyr Lys Arg Arg Phe His Glu
1               5                   10                  15

Lys His His Ser His Arg Gly Tyr
            20

<210> SEQ ID NO 7
<211> LENGTH: 24
<212> TYPE: PRT
<213> ORGANISM: Artificial sequence
<220> FEATURE:
<222> LOCATION: 13
<223> OTHER INFORMATION: Sequence of Histatin-5 peptide substituted with
      a Leu at position 13

<400> SEQUENCE: 7

Asp Ser His Ala Lys Arg His His Gly Tyr Lys Arg Leu Phe His Glu
1               5                   10                  15

Lys His His Ser His Arg Gly Tyr
            20

<210> SEQ ID NO 8
<211> LENGTH: 24
<212> TYPE: PRT
<213> ORGANISM: Artificial sequence
<220> FEATURE:
<222> LOCATION: 17
<223> OTHER INFORMATION: Sequence of Histatin-5 peptide substituted with
      an Arg at position 17

<400> SEQUENCE: 8

Asp Ser His Ala Lys Arg His His Gly Tyr Lys Arg Lys Phe His Glu
1               5                   10                  15

Arg His His Ser His Arg Gly Tyr
            20

<210> SEQ ID NO 9
<211> LENGTH: 24
<212> TYPE: PRT
<213> ORGANISM: Artificial sequence
<220> FEATURE:
<222> LOCATION: 17
<223> OTHER INFORMATION: Sequence of Histatin-5 peptide substituted with
      a Leu at position 17

<400> SEQUENCE: 9

Asp Ser His Ala Lys Arg His His Gly Tyr Lys Arg Lys Phe His Glu
1               5                   10                  15
```

Leu His His Ser His Arg Gly Tyr
            20

<210> SEQ ID NO 10
<211> LENGTH: 24
<212> TYPE: PRT
<213> ORGANISM: Artificial sequence
<220> FEATURE:
<222> LOCATION: 11, 17
<223> OTHER INFORMATION: Sequence of Histatin-5 peptide substituted with
      an Arg at positions 11 and 17

<400> SEQUENCE: 10

Asp Ser His Ala Lys Arg His His Gly Tyr Arg Arg Lys Phe His Glu
1               5                   10                  15

Arg His His Ser His Arg Gly Tyr
            20

<210> SEQ ID NO 11
<211> LENGTH: 24
<212> TYPE: PRT
<213> ORGANISM: Artificial sequence
<220> FEATURE:
<222> LOCATION: 16
<223> OTHER INFORMATION: Sequence of Histatin-5 peptide substituted with
      an Arg at position 16

<400> SEQUENCE: 11

Asp Ser His Ala Lys Arg His His Gly Tyr Lys Arg Lys Phe His Arg
1               5                   10                  15

Lys His His Ser His Arg Gly Tyr
            20

<210> SEQ ID NO 12
<211> LENGTH: 24
<212> TYPE: PRT
<213> ORGANISM: Artificial sequence
<220> FEATURE:
<222> LOCATION: 16
<223> OTHER INFORMATION: Sequence of Histatin-5 peptide substituted with
      a Leu at position 16

<400> SEQUENCE: 12

Asp Ser His Ala Lys Arg His His Gly Tyr Lys Arg Lys Phe His Leu
1               5                   10                  15

Lys His His Ser His Arg Gly Tyr
            20

<210> SEQ ID NO 13
<211> LENGTH: 24
<212> TYPE: PRT
<213> ORGANISM: Artificial sequence
<220> FEATURE:
<222> LOCATION: 13
<223> OTHER INFORMATION: Sequence of Histatin-5 peptide substituted with
      a Glu at position 13

<400> SEQUENCE: 13

Asp Ser His Ala Lys Arg His His Gly Tyr Lys Arg Glu Phe His Glu
1               5                   10                  15

Lys His His Ser His Arg Gly Tyr
            20

<210> SEQ ID NO 14
<211> LENGTH: 24

```
<212> TYPE: PRT
<213> ORGANISM: Artificial sequence
<220> FEATURE:
<222> LOCATION: 13
<223> OTHER INFORMATION: Sequence of Histatin-5 peptide substituted with
      a His at position 13

<400> SEQUENCE: 14

Asp Ser His Ala Lys Arg His His Gly Tyr Lys Arg His Phe His Glu
1               5                   10                  15

Lys His His Ser His Arg Gly Tyr
            20
```

HISTATIN-5 BASED SYNTHETIC PEPTIDES AND USES THEREOF

CROSS-REFERENCE TO RELATED APPLICATIONS

This non-provisional application claims benefit of priority under 35 U.S.C. § 119(e) of provisional U.S. application Ser. No. 62/480,054, filed Mar. 31, 2017, and of provisional U.S. application Ser. No. 62/320,675, filed Apr. 11, 2016, the entirety of both of which are hereby incorporated by reference.

BACKGROUND OF THE INVENTION

Field of the Invention

The invention relates generally to the field of medicine, microbiology, and molecular biology. In particular, the invention relates to Histatin-5 based peptides that are useful in a spectrum of applications, including antifungal, antibacterial, anti-inflammatory and immunomodulatory applications. The Histatin-5 based peptides described herein can be formulated in bioadhesive hydrogel formulations.

Description of the Related Art

There are a variety of defense mechanisms which are operative in the oral activity including but not limited to the innate nonimmune proteins and peptides which are of salivary gland origin. One group of such proteins are the histatins which are a family of small, histidine-rich, cationic peptides secreted by the human parotid and submandibular glands. The mode of action of histatins is distinct from those exhibited by the conventional azole and polyene drugs.

One of the members of the histatin group, Histatin-5 (Hst-5), has been shown to have significant antifungal activity for *Candida albicans* and related fungal organisms as well as activity against different bacterial species. The important role of these innate antimicrobials in the protection of the oral cavity from the constant exposure to microbial challenges is only just beginning to be understood and appreciated. It is appreciated that Hst-5 is unique as it is potent in killing *C. albicans*, including strains resistant to common antifungals, and importantly, does not induce resistance.

*Candida albicans* is a commensal fungus commonly colonizing human mucosal surfaces. *C. albicans* can become a pathogen causing recurrent infections. In particular, Pseudomembranous candidiasis (thrush) is the most common opportunistic infection in HIV patients. Additionally, cancer patients receiving immunosuppressive therapy and radiotherapy for head and neck cancers are particularly vulnerable to candidiasis. Also, *Candida*-associated stomatitis is the most common form of oral *Candida* infection occurring in about 70% of denture wearers. Denture stomatitis is characterized by localized inflammation of the denture bearing mucosa which is difficult to treat often causing severe pain affecting the ability to speak and eat. This chronic disease unequivocally involves adherence and biofilm formation of *C. albicans* on denture acrylic surfaces. Despite, antifungal therapy, infection is often re-established soon after treatment occurs. Additionally, *Candida* is a common cause of gingivitis in individuals infected with HIV. Hst-5 therapy may be an option to treat and prevent gingivitis and reduce *Candida* growth in the oral cavity. Therefore, it has become critical to identify alternative therapeutic agents to aid in preventing and ameliorating these common, chronic, and recurrent infections.

In *C. albicans*, the transition from harmless commensal to pathogen is finely balanced and attributable to a repertoire of virulence determinants and its aptitude to adapt and evade the host immune response. Previous work has shown that *C. albicans* has the ability to degrade and deactivate Histatin-5 via a secreted proteolytic enzyme pointing to a novel immune evasion strategy for *C. albicans* that may be involved in its transition from commensal to pathogen. The ability of *C. albicans* to degrade Hst-5 was found to be proportional to its cell density and inversely proportional to Hst-5 concentration affirming that maintenance of oral health is highly dependent on the fine balance between pathogen and host innate immune function. Interestingly, Hst-5 has been shown to clear existing lesions in the oral cavity as well as associated tissue inflammation. Coupled with the lack of toxicity, anti-inflammatory and wound healing properties, Hst-5 is recognized as an important therapeutic agent.

There is a clear need to identify novel antibacterial and antifungal agents which can be used to maintain good oral health and in the development of novel bioadhesive gel type formulations which include these novel agents, such as Hst-5 and derivatives thereof, for use in the prevention and treatment of oral candidiasis as well as for applications for treating and preventing other disease conditions caused by bacteria and fungi in the human host. The present invention fulfills this longstanding need and desire in the art.

SUMMARY OF THE INVENTION

The present invention is directed to a synthetic peptide or synthetic fragment thereof. The synthetic peptide or a fragment comprises a Histatin-5 peptide sequence with at least one amino acid substitution therein. The present invention is directed to a related a synthetic peptide or synthetic fragment thereof where the at least one amino acid substitution is a lysine and/or glutamic acid to an arginine and/or a leucine. The present invention is directed to another related a synthetic peptide or synthetic fragment thereof further comprising an agent to improve uptake of the peptide or fragment conjugated thereto.

The present invention also is directed to a pharmaceutical formulation. The pharmaceutical formulation comprises the synthetic peptide or synthetic fragment thereof described herein and a biocompatible gelling agent. The present invention is directed to a related pharmaceutical formulation further comprising at least one antifungal agent or at least one antibacterial agent or a combination thereof.

The present invention is directed further to a method for treating or preventing a pathophysiological condition in a subject in need thereof. The method comprises administering topically one or more times the pharmaceutical formulation described herein to the subject.

The present invention is directed further still to a synthetic peptide resistant to proteolysis by *Candida albicans* enzymes. The synthetic peptide has a sequence shown in SEQ ID NO: 2, SEQ ID NO: 3, SEQ ID NO: 4, SEQ ID NO: 5, SEQ ID NO: 7, SEQ ID NO: 8, SEQ ID NO: 9, SEQ ID NO: 10, SEQ ID NO: 11, or SEQ ID NO: 12.

The present invention is directed further still to a method for treating or preventing an oral infection associated with a *Candida* sp. in a subject in need thereof. The method comprises administering topically one or more times a hydrogel comprising at least one of the synthetic peptides described herein to the subject. The present invention is directed to a related method in which the hydrogel further comprises one or more antifungal agents.

Other and further aspects, features, and advantages of the present invention will be apparent from the following description of the presently preferred embodiments of the invention. These embodiments are given for the purpose of disclosure.

BRIEF DESCRIPTION OF THE DRAWINGS

So that the matter in which the above-recited features, advantages and objects of the invention, as well as others that will become clear, are attained and can be understood in detail, more particular descriptions of the invention briefly summarized above may be by reference to certain embodiments thereof that are illustrated in the appended drawings. These drawings form a part of the specification. It is to be noted, however, that the appended drawings illustrate preferred embodiments of the invention and therefore are not to be considered limiting in their scope.

FIGS. 6A, 6D: All peptides with Sap9 and Sap2; FIGS. 6B, 6E: Arginine peptides with and without Sap9 and Sap2; FIGS. 6C, 6F: Leucine peptides with and without Sap9 and Sap2.

DETAILED DESCRIPTION OF THE INVENTION

Figure 1A:
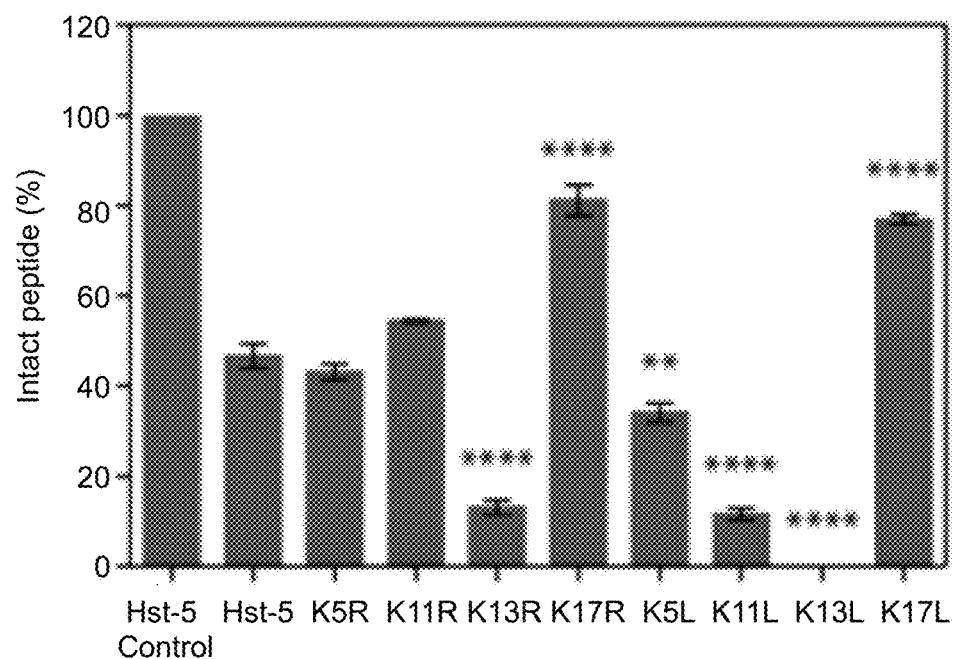
FIGS. 1A-1I show the degradation of parent Hst-5 and Hst-5 synthetic peptides by purified Sap9 (FIGS. 1A-1B, 1E-1F), Sap2 (FIGS. 1C-1D, 1G-1H) and Sap10 (FIG. 1I). The peptides (150 μg mL$^{-1}$) and Saps (3.13 μg mL$^{-1}$ Sap9 and 6.25 μg mL$^{-1}$ Sap2) were incubated for 2 h at 37° C. Samples were run on a gel (FIGS. 1B, 1D, 1F, 1H-1I), and the amount of intact peptide was quantified by densitometry to compare the amount of intact peptide (upper band) to the peptide fragments. Error bars represent standard error of the mean (n=3). The asterisks indicate the level of statistical significance against parent Hst-5 incubated with the Saps. The lower band in the Hst-5 control lanes is due to Coomassie dye.

As used herein in the specification, "a" or "an" may mean one or more. As used herein in the claim(s), when used in conjunction with the word "comprising", the words "a" or "an" may mean one or more than one.

As used herein "another" or "other" may mean at least a second or more of the same or different claim element or components thereof. Similarly, the word "or" is intended to include "and" unless the context clearly indicates otherwise. "Comprise" means "include."

As used herein, the term "about" refers to a numeric value, including, for example, whole numbers, fractions, and percentages, whether or not explicitly indicated. The term "about" generally refers to a range of numerical values (e.g., +/−5-10% of the recited value) that one of ordinary skill in the art would consider equivalent to the recited value (e.g., having the same function or result). In some instances, the term "about" may include numerical values that are rounded to the nearest significant figure.

As used herein, the term "subject" refers to a human or non-human mammal.

In one embodiment of the present invention there is provided a synthetic peptide or synthetic fragment thereof, comprising a Histatin-5 peptide sequence with at least one amino acid substitution therein. Further to this embodiment the synthetic peptide or synthetic fragment thereof may comprise an agent to improve uptake of the peptide or fragment conjugated thereto. A representative example of the uptake agent is spermidine or a polymeric delivery agent.

In both embodiments the Histatin-5 peptide sequence may be DSHAKRHHGYKRKFHEKHHSHRGY (SEQ ID NO: 1).

In one aspect of both embodiments the synthetic fragment may comprise an amino acid substitution at positions 5, 11, 13, 16, or 17 of the Histatin-5 peptide sequence or a combination thereof. Particularly in this aspect the synthetic peptide fragment may comprise an amino acid substitution at position 16 or 17 or a combination thereof. Also in this aspect the amino acid substitution at the position(s) may be an arginine or a leucine.

In another aspect of both embodiments the synthetic peptide may comprise at least one substitution at a lysine residue or a substitution at a glutamic acid residue or a combination thereof. In this aspect the synthetic peptide may comprise a lysine to arginine substitution or a lysine to leucine substitution or a combination thereof. Particularly, the amino acid substitution may be K5R (SEQ ID NO: 2), K5L (SEQ ID NO: 3), K11R (SEQ ID NO: 4), K11L (SEQ ID NO: 5), K13R (SEQ ID NO: 6), K13L (SEQ ID NO: 7), K17R (SEQ ID NO: 8), K17L (SEQ ID NO: 9), or K11R-K17R (SEQ ID NO: 10). Also in this aspect the glutamic acid substitution may be glutamic acid to arginine or glutamic acid to leucine. Particularly, the amino acid substitution may be E16R (SEQ ID NO: 11) or E16L (SEQ ID NO: 12).

In another embodiment of the present invention, there is provided a pharmaceutical formulation, comprising the synthetic peptide or synthetic fragment thereof of described supra and a biocompatible gelling agent. Further to this embodiment the pharmaceutical formulation may comprise at least one antifungal agent or at least one antibacterial agent or a combination thereof.

In both embodiments the gelling agent may have a concentration of at least 4% in the pharmaceutical formulation. Also in both embodiments the pharmaceutical formulation may be a bioadhesive hydrogel. In addition the bioadhesive hydrogel may be coated onto a bandage or a wound dressing or is directly coatable onto a tissue, teeth, or an oral appliance.

In yet another embodiment of the present invention there is provided a method for treating or preventing a pathophysiological condition in a subject in need thereof, comprising administering topically one or more times the pharmaceutical formulation of as described supra to the subject.

In this embodiment the pathophysiological condition may be a fungal infection or a bacterial infection or inflammation associated therewith. Representative fungal species causative of the infection or associated inflammation may be an *Aspergillus* sp., a *Blastomyces* sp., a *Candida* sp., a *Cryptococcus* sp., a *Histoplasma* sp., a *Coccidiodes* sp., or a *Pneumocystis* sp. Representative bacteria causative of the infection or associated inflammation may be *Staphylococcus aureus, Streptococcus mutans, Porphyromonas gingivalis, Fusobacerium nucleatum*. Also in this embodiment the pathophysiological condition may be chronic mucositis, a chronic cutaneous condition, or impaired healing in a diabetic subject.

In yet another embodiment of the present invention there is provided a synthetic peptide resistant to proteolysis by *Candida albicans* enzymes having a sequence shown in SEQ ID NO: 2, SEQ ID NO: 3, SEQ ID NO: 4, SEQ ID NO: 5, SEQ ID NO: 7, SEQ ID NO: 8, SEQ ID NO: 9, SEQ ID NO: 10, SEQ ID NO: 11, or SEQ ID NO: 12. Further to this embodiment the synthetic peptide may comprise an agent to improve uptake of the synthetic peptide conjugated thereto. A representative example of the agent is spermidine or a polymeric delivery agent.

In yet another embodiment of the present invention there is provided a method for treating or preventing an oral infection associated with a *Candida* sp. in a subject in need thereof, comprising administering topically one or more times a hydrogel comprising at least one of the synthetic peptides as described supra to the subject. Further to this embodiment the hydrogel may comprise one or more antifungal agents. In both embodiments the hydrogel may be a bioadesive hydrogel. Also in both embodiments the *Candida* sp. may be *Candida albicans*.

Provided herein are synthetic peptides based on an Hst-5 peptide sequence such as the sequence shown in SEQ ID NO: 1. The synthetic peptides comprise at least one substitution, for example, at a lysine residue or a glutamic acid residue. It is demonstrated herein that changing a one or two of these residues in the Hst-5 sequence can significantly alter its proteolysis by purified secreted aspartic proteases Sap9 and Sap2, as well as by whole *Candida albicans* cells, in increasing resistance to degradation by these enzymes. Furthermore, the effects of the modifications are site-, residue-, or Sap-dependent, and the substitutions affect not only cleavage at the substitution sites, but also the degradation of the peptide as a whole. The present invention provides peptide engineering approaches, as described in the Examples, that can be used to design more robust peptides in the presence of aspartic proteases, as potential therapeutics to treat fungal infections.

Particularly, the synthetic Hst-5 peptide may comprise an amino acid which can carry a positive charge or no charge at one or more of the naturally occurring lysine (K) residues, such as an arginine (R) or a leucine (L) amino acid. For example, the naturally occurring lysine residues at positions 5, 11, 13, and/or 17 may be replaced with an arginine or a leucine. Also, the synthetic Hst-5 peptide may comprise an arginine or leucine at the naturally occurring glutamic acid at position 16. The synthetic peptide may be a synthetic fragment of the Hst-5 peptide that contains at least one of the substituted positions at residues 5, 11, 13, 16, or 17 to retain antifungal activity. Preferably, the synthetic peptide or fragment thereof comprises a substitution at residues 16 and/or 17. Moreover, the synthetic peptides may be conjugated with an agent to improve uptake of the peptide by the pathogen such as, but not limited to, spermidine or polymer useful as a delivery agent.

As such, provided herein are pharmaceutical formulations comprising one or more of the synthetic peptides and/or synthetic fragments thereof and a biocompatible gelling agent, for example, a gelling polymer such as, hydroxypropyl methycellulose (HPMC). Alternatively, the pharmaceutical formulation further may comprise other antifungal and/or antibacterial agents. In a non-limiting example, pharmaceutical formulation is a hydrogel. Optionally, the hydrogel may contain adhesive polymers, as a bioadhesive hydrogel, suitable for topical application or included in a dressing or a wound covering or to enable the hydrogel to stay in place when coated directly onto a tissue, teeth, periodontium, the oral mucosa, or onto an oral appliance, such as a denture. The composition of and making of gels or hydrogels and the incorporation of a bioactive substance therein is well-known in the art, for example as previously described (1).

The synthetic peptides and synthetic peptide fragments thereof disclosed herein are well-suited as therapeutic and prophylactic agents. A gel formulation of one or more synthetic peptides and/or synthetic fragments is useful as an antimicrobial, anti-inflammatory, tissue regenerative, and/or wound healing therapeutic or as an immunomodulating agent. Particularly, the synthetics peptides and gel formulation thereof maintain the overall integrity of oral, mucosal and other tissues. The synthetic peptides, fragments thereof or gel formulations are useful to treat or prevent microbial infections, for example, fungal or bacterial infections, including inflammatory responses following infection, to promote wound healing or to treat chronic pathophysiological conditions such as mucositis, impaired healing in diabetics and cutaneous conditions, for example, psoriasis. For example, the synthetic peptides are bioactive against fungal microbes, such as commensal and opportunistic pathogens, for example, but not limited to, *Aspergillus, Blastomyces, Candida, Cryptococcus, Histoplasma, Coccidiodes*, or *Pneumocystis* species and against bacterial pathogens, for example, but not limited to *Staphylococcus aureus, Streptococcus mutans, Porphyromonas gingivalis, Fusobacerium nucleatum*.

Thus, provided herein are methods for treating or preventing a pathophysiological condition associated with a fungal or bacterial infection in a subject in need of such treatment or prophylaxis. Also provided are methods for treating a chronic pathophysiological condition or a wound or lesion produced by the same. In a non-limiting example, the fungal or bacterial infection, wound or lesion occurs in the oral cavity, including the tongue, periodontium, teeth, or oral mucosa or caused by dentures or other oral appliance worn by a subject. The methods described herein may incorporate other antifungal and/or antibacterial agents, either separately or in combination with the synthetic peptides or synthetic peptide fragments thereof in the hydrogel, as are known in the art and effective against a particular pathophysiological condition. Treatment with the synthetic peptides and/or synthetic peptide fragments is useful against fungal microbes that have become resistant to first-line and second-line antifungals. Particularly, the pathophysiological condition is responsive to a topical application of the synthetic peptides or a gel formulation, such as a hydrogel or adhesive hydrogel. One of skill in this art would is well able to determine the amount of synthetic peptides to administer or a regimen for such topical administration based on the pathophysiological condition and the subject in need of this treatment or prophylaxis.

The following examples are given for the purpose of illustrating various embodiments of the invention and are not meant to limit the present invention in any fashion.

Example 1

Materials and Methods
Peptides and Enzymes

The parent Hst-5 peptide and the synthetic peptides in Table 1 were synthesized by GenScript with a purity ≥95%, and trifluoroacetic acid salt removal to hydrochloride. Purified Sap2 and Sap9 were obtained by B. Hube from Friedrich Schiller University, Germany. The Saps were produced in *Pichia pastoris*, as described (2) and Sap9 was produced without its GPI anchor (3). The proteolytic activities of the Saps were confirmed using the EnzChek Protease Assay Kit (ThermoFisher Scientific).

Proteolytic Degradation of the Peptides

To study the interaction of Hst-5 with *C. albicans* Saps, the proteolysis of Hst-5 and eight synthetic peptides by Sap2 and Sap9, which substantially cleaved Hst-5 consistent with the findings from previous work (4), was evaluated. The design of the Hst-5 synthetic peptides focused on the four lysine residues and the glutamic acid residue in the peptide, as it was observed that lysine residues are prominent at the reported cleavage sites of Hst-5 with Saps or *C. albicans* cells. These lysine residues are important for the recognition or cleavage of Hst-5 and each of the lysine residues is replaced with either an arginine or a leucine (Table 1). Arginine was selected to preserve the positive charge when substituted for lysine, as the cationic nature of antimicrobial peptides often plays a role in their function. Leucine was selected to evaluate removal of the positive charge at each site, which could affect the interaction of the peptides with the aspartic acid residues at the active site of the Saps. The glutamic acid residue was selected to evaluate the effect of removing a negative charge near a key site, i.e., lysine, on proteolytic cleavage. Substitutions are shown in bold.

TABLE 1

Hst-5 peptide substitutions at lysine and glutamic acid residues

| Peptide | Hst-5 substitutions (bold) | SEQ ID NOs |
| --- | --- | --- |
| Hst-5 | DSHAKRHHGYKRKFHEKHHSHRGY | SEQ ID NO: 1 |
| K5R | DSHARRHHGYKRKFHEKHHSHRGY | SEQ ID NO: 2 |
| K5L | DSHALRHHGYKRKFHEKHHSHRGY | SEQ ID NO: 3 |
| K11R | DSHAKRHHGYRRKFHEKHHSHRGY | SEQ ID NO: 4 |
| K11L | DSHAKRHHGYLRKFHEKHHSHRGY | SEQ ID NO: 5 |
| K13R | DSHAKRHHGYKRRFHEKHHSHRGY | SEQ ID NO: 6 |
| K13L | DSHAKRHHGYKRLFHEKHHSHRGY | SEQ ID NO: 7 |
| K17R | DSHAKRHHGYKRKFHERHHSHRGY | SEQ ID NO: 8 |
| K17L | DSHAKRHHGYKRKFHELHHSHRGY | SEQ ID NO: 9 |
| K11R-K17R | DSHAKRHHGYRRKFHERHHSHRGY | SEQ ID NO: 10 |
| E16R | DSHAKRHHGYKRKFHRKHHSHRGY | SEQ ID NO: 11 |
| E16L | DSHAKRHHGYKRKFHLKHHSHRGY | SEQ ID NO: 12 |
| K13E, control | DSHAKRHHGYKREFHEKHHSHRGY | SEQ ID NO: 13 |
| K13H, control | DSHAKRHHGYKRHFHEKHHSHRGY | SEQ ID NO: 14 |

To determine the extent of degradation of the peptides by the Saps, Hst-5 and the Hst-5 synthetic peptides were each mixed with Sap9 or Sap2 at final concentrations of 150 μg mL$^{-1}$ peptide and 3.13 μg mL$^{-1}$ or 6.25 μg mL$^{-1}$ protease for Sap9 or Sap2, respectively. Experiments were done in 1 mM NaPB. The mixtures were incubated at 37° C. for 2 h, and NaPB with no Sap was used as a control. After the incubation, the samples were mixed with tricine sample buffer (without Coomassie Blue G-250, except in control samples) containing β-mercaptoethanol and boiled for 5 min at 100° C. to inactivate the proteases. The degraded and non-degraded peptides were separated by gel electrophoresis in 10-20% Tris-tricine gels (Bio-Rad), and the gels were then fixed in a 10% acetic acid/40% methanol/50% water mixture for 30 min. The fixed gels were stained with Bio-Safe Coomassie stain (Bio-Rad) for 1 h and washed with fresh water three times, once overnight and then twice for at least 2 h each time. The gels were imaged on a Chemidoc imager (Bio-Rad), and densitometric analysis was done with Image Lab software (Bio-Rad). In the analysis, the upper band was taken as intact peptide and the lower band was taken as degraded products. Three replicates of the assay were done.

For degradation with *C. albicans*, a single colony of the ATCC 90028 strain (American Type Culture Collection) was used to inoculate YPD. The culture was grown overnight, subcultured, and grown to an optical density of 1-1.2 at $OD_{600}$. All incubations were done at 30° C. The cells were washed three times in 100 mM NaPB and diluted to $2\times10^9$ cells $mL^{-1}$. Equal volumes of cells and peptides were mixed and incubated for 2 h at 37° C. The cells were removed by centrifugation, and the supernatants were mixed with tricine sample buffer and boiled for 10 min. The samples were then run on gels and analyzed as described above for degradation by the Saps. Three biological replicates were performed.

For statistical analysis, one-way ANOVA tests were performed with p<0.05 and Dunett's multiple comparison tests with the Hst-5 sample as the control. The number of asterisks indicates the level of statistical significance: * for p<0.05,  for p<0.01, * for p<0.001, and **** for p<0.0001.

Antifungal Activity Assay

The anti-*Candida* activities of the intact peptides were assessed by an antifungal activity assay. As described above for the degradation assay, an overnight culture of *C. albicans* was subcultured and grown in YPD media. Cells were washed three times in 2 mM NaPB and diluted to $5\times10^5$ cells $mL^{-1}$ or $5\times10^7$ cells $mL^{-1}$. Serial dilutions (0-100 μM for the lower cell density and 0-400 μM for the higher cell density) of parent Hst-5 and the Hst-5 synthetic peptides were prepared in water, and 20 μL of the peptides and 20 μL of the cells were mixed and incubated in round-bottom 96-well culture plates for 30 min at 30° C. After incubation, 320 μL of 1 mM NaPB was loaded into each well to stop additional killing of the cells by the peptides. Mixtures were further diluted and approximately 250 cells were inoculated into round-bottom culture plates with equal volumes of YPD media and 1 mM NaPB at a total volume of 200 μL. Wells containing only YPD and NaPB were served as a sterility control and provided measurements for the background signal. The $OD_{600}$ was measured after overnight incubation on a microplate shaker at 30° C. The reduction in viability was calculated as $$\% \text{ reduction in viability} = \left[1 - \frac{(OD_{\text{with peptide}} - OD_{\text{background}})}{(OD_{\text{no peptide}} - OD_{\text{background}})}\right] \times 100$$

Three biological replicates were performed on separate days, with two replicates on each day.

To measure the antifungal activity of the peptides following degradation by the Saps, the antifungal activity assay was performed as described above, except the peptides were first exposed to Saps. The peptide fragments were prepared by incubating each peptide (150 μg $mL^{-1}$) with 6.25 μg $mL^{-1}$ Sap9 or 18 μg $mL^{-1}$ Sap2 for 2 h at 37° C. The enzymes were then inactivated by heating at 100° C. for 5 min. As controls, each peptide was also incubated with only NaPB buffer. Samples were then stored at −20° C. until use in the antifungal activity assay.

MS/MS Analysis

The cleavage sites of the Saps and the abundance of the fragments produced by cleavage were determined using mass spectrometry. After incubation with 3.13 μg $mL^{-1}$ Sap9 or 6.25 μg $mL^{-1}$ Sap2 and heat inactivation of the Saps, 25 μL of each sample was desalted using a C-18 TopTip micro-spin column (Glygen Corp.) following the manufacturer's protocol. The binding solution was 0.1% formic acid, and the releasing solution was 0.1% formic acid/60% acetonitrile (ACN). To ensure equal flow-through volume of each sample, 18 μL of desalted sample was aliquoted and 1 μL of the four-amino acid peptide MRFA at 0.1 mg $mL^{-1}$ was added. Samples were manually loaded through loop injection at 25 μL $min^{-1}$ with 40% ACN/0.1% formic acid. Mass spectra were acquired with a Thermo Scientific Orbitrap Fusion Lumos Tribrid mass spectrometer with data-dependent analysis at a 5 s cycle time. Manufacturer recommended source parameters for a flow rate of 25 μL $min^{-1}$ were applied. Full scan mass spectra of m $z^{-1}$ 350-1550 were acquired in the orbitrap at R=120000 (m $z^{-1}$ 200) with fluoranthene ion as the internal calibrant. CID and ETD fragments of the most intense ions (z>1) were recorded with the orbitrap at R=60000 (m $z^{-1}$ 200). Dynamic exclusion was set at 30 s.

The molecular weights of the peptides and their fragments were calculated from full scan MS spectra using the XTract program in the XCalibur software (Thermo Scientific). MS/MS spectra from ETD and CID fragmentation were processed using Proteome Discoverer (V2.1) with Prosight PD node to identify peptides and their degradation products. The database was the collection of Hst-5 and its analogs used in this study. Intensities of identified peptides and their degradation products relative to the internal standard MRFA were obtained from the deconvoluted full scan mass spectra.

Example 2

Proteolysis of Lysine Substituted Peptides
Lysine Substitutions Modulate Susceptibility to Proteolysis by Purified Saps To determine whether the single-residue replacement has an effect on the overall degradation of Hst-5, Hst-5 and each modified peptide was tested with purified recombinant Sap9 and Sap2. Hst-5 and each synthetic peptide in Table 1 were incubated with or without 3.13 μg $mL^{-1}$ Sap9 or 6.25 μg $mL^{-1}$ Sap2 for 2 h at 37° C. in 1 mM sodium phosphate buffer (NaPB). The intact peptide was then separated from the degradation products using gel electrophoresis and quantified the level of degradation using densitometric analysis of Coomassie-stained gels. Both arginine and leucine substitutions at the K17 site led to a dramatic decrease in degradation by Sap9 and Sap2. Following incubation with Sap9, 82% and 77% of K17R and K17L, respectively, remained intact compared to 47% of Hst-5 (FIG. 1A). No detectable degradation of the K17R and K17L synthetic peptides was visible after incubation with Sap2, while only 61% of the parent Hst-5 peptide remained intact (FIG. 1C).

With the exception of the K17 residue, modification of lysine residues to leucine made the Hst-5 synthetic peptides more susceptible to degradation by Sap9. The K5L, K11L, and K13L peptides all showed greater degradation than their arginine-substituted counterparts or parent Hst-5 (FIG. 1A). In fact, the K13L peptide was degraded to the extent that no intact peptide could be detected on the gel. No detectable degradation of the peptides was visible after incubation with Sap10 (FIG. 1E).

Figure 1B:
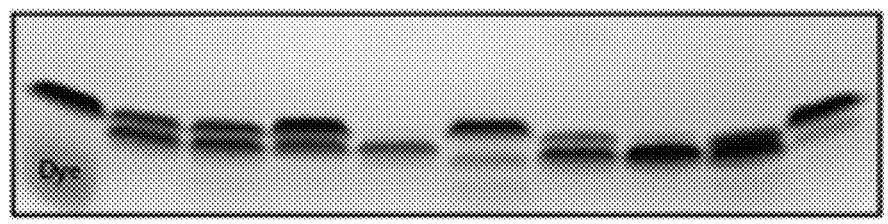
Figure 1C:
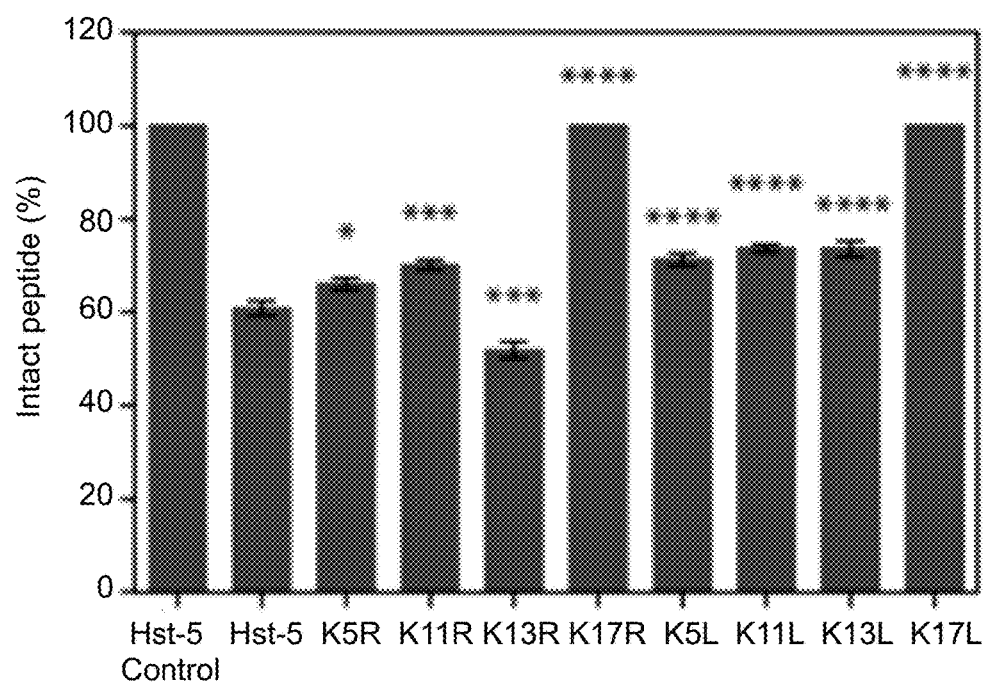
Figure 1D:
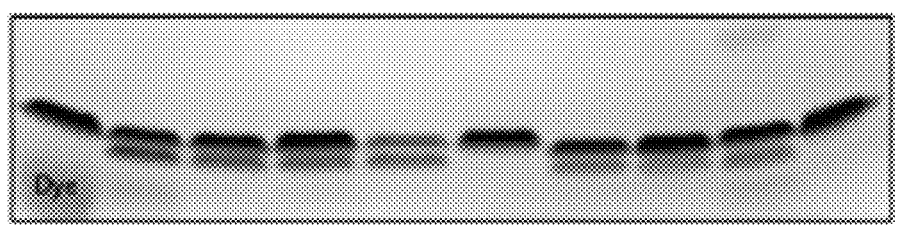
Figure 1E:
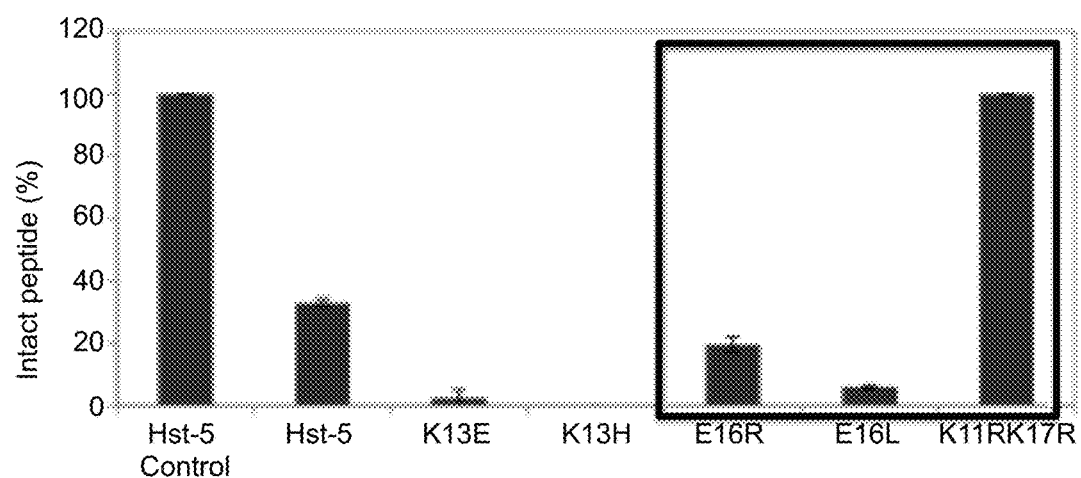
Figure 1F:
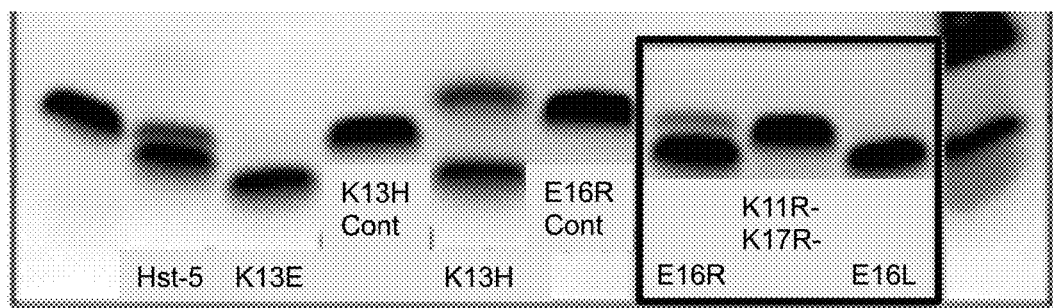
Figure 1G:
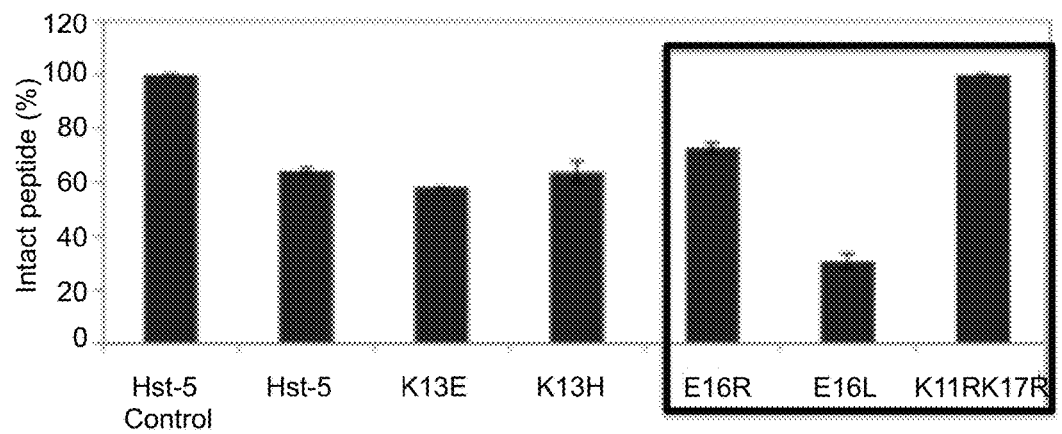
Figure 1H:
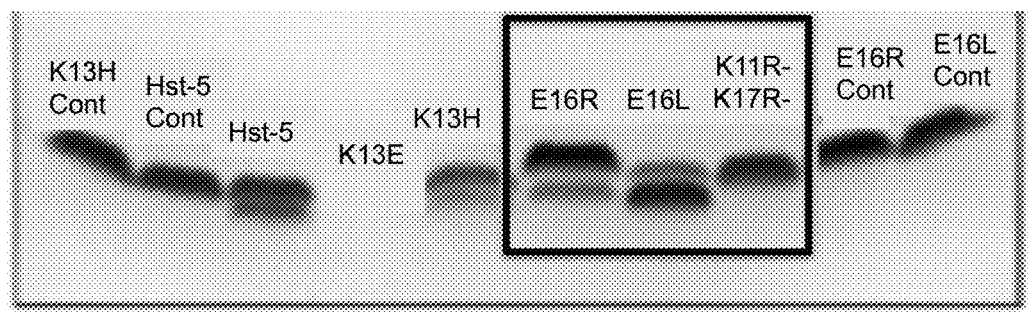
Figure 1I:
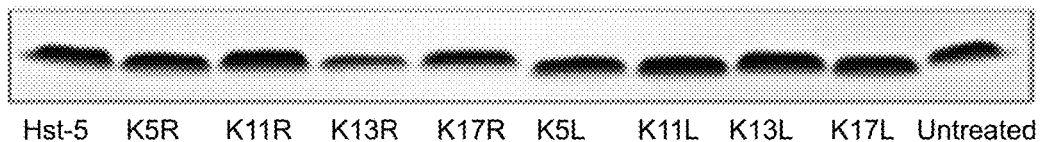

In terms of proteolytic resistance, the K11R-K17R peptide shows no observable degradation by either *C. albicans* secreted aspartic proteases (Saps) (FIGS. 1E, 1G). This is true for both Sap9 and Sap2. The E16R and E16L synthetic peptides show degradation levels similar to the parent Hst-5 (E16R) or increased compared to Hst-5 (E16L).

While leucine substitutions resulted in more proteolysis of the modified peptides by Sap9, they led to a decrease in proteolysis by Sap2 (FIG. 1C). With the exception of K13R, all of the Hst-5 synthetic peptides exhibited a decrease in degradation compared to the parent Hst-5 after incubation with Sap2. These results demonstrate the ability to easily detect changes in a peptide's susceptibility to proteolysis by gel electrophoresis (FIGS. 1B, 1D, 1F, 1H-1I) and indicate that this approach is feasible for exploring how aspartic proteases interact with antimicrobial peptides.

Proteolysis by C. albicans Cells is Comparable to Proteolysis by Purified Saps

Figure 2A:
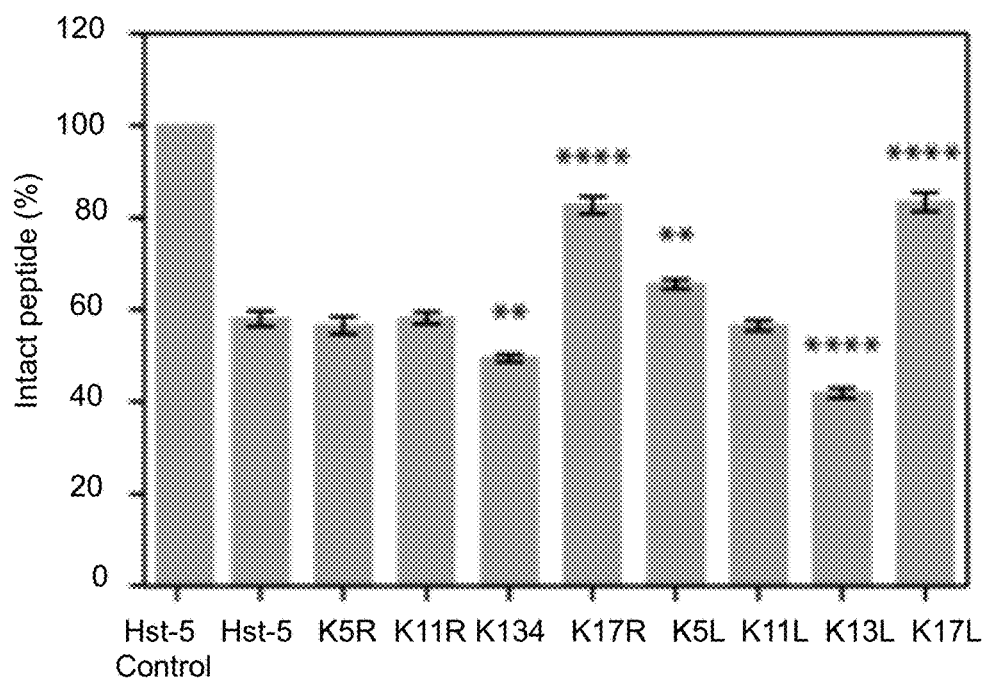
FIGS. 2A-2B show the degradation of parent Hst-5 and Hst-5 peptides with lysine substituted with arginine or leucine by *C. albicans*. The peptides (150 μg mL$^{-1}$) and *C. albicans* (1×10$^9$ cells mL$^{-1}$) were incubated for 2 h at 37° C. Samples were run on a gel (FIG. 2B), and the amount of intact peptide (FIG. 2A) was quantified by densitometry to compare the amount of intact peptide (upper band) to the peptide fragments. Error bars represent standard error of the mean (n=3). The asterisks indicate the level of statistical significance against parent Hst-5 incubated with cells. The lower band in Hst-5 control lane is due to Coomassie dye.
Figure 2B:
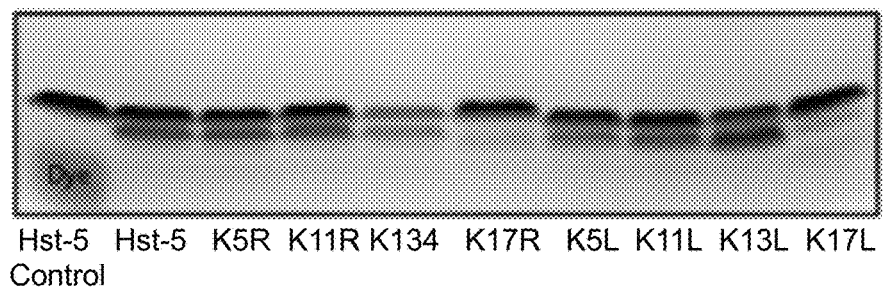

After observing the effect of residue modifications on the cleavage of Hst-5 by the purified recombinant Saps, whether incubation of the peptides with whole C. albicans cells expressing Saps (rather than Saps produced recombinantly) would yield similar results was evaluated. Hst-5 and the synthetic peptides were incubated with C. albicans cells for 2 h at 37° C. in 100 mM NaPB. The high ionic strength of this buffer prevents internalization of the peptides by C. albicans (4) allowing analysis of degradation of the peptides without the confounding effects of peptide internalization, which would reduce the amount of peptide in the reaction buffer. Following incubation with the cells, the peptide samples were run on a gel and stained, and densitometric analysis revealed a pattern that exhibits characteristics of the results observed with the individual Saps (FIGS. 2A-2B).

As seen with the results for purified Sap9 and Sap2, both K17 modifications resulted in an increase in the amount of intact peptide remaining. The results for the K13L peptide followed the Sap9 proteolysis pattern, with an increase in degradation compared to the parent Hst-5. The peptides with modifications at K5 showed a mixed pattern, with a decrease in proteolysis for K5L emulating the Sap2 result and no significant effect for K5R emulating the Sap9 result. These outcomes demonstrate results that follow the effects of both the cell-wall anchored Sap9 and the fully secreted Sap2. It is important to note that additional Saps are likely to be present in the cell-based degradation assay and could contribute to the observed degradation. However, the overall results with the purified Saps are in line with the results observed with the fungal cells, indicating that using purified Saps is a reasonable approach for studying biologically relevant effects of peptide sequence on susceptibility to Saps produced by cells.

Example 3

Mass Spectrometry Confirms the Effects of Lysine Modifications

To gain a more in-depth understanding of how the modifications to the peptide sequence affect the cleavage of Hst-5 by Saps, mass spectrometry was used to determine the cleavage sites and the abundance of peptide fragments. After incubation of the peptides with each Sap, the four-amino-acid peptide MRFA was added as an internal standard, and samples were directly injected into the mass spectrometer.

Mass spectrometry of the parent Hst-5 peptide incubated with Sap9 showed that the signal for the degradation fragment containing amino acids 1-17 of Hst-5 was higher than the intact peptide (FIGS. 3A-3I). Cleavage was observed at the N- and C-terminal side of K13 and the C-terminal side of K17, which are cleavage sites that have been previously reported for Sap9 and Sap2 (4-5). No cleavage was seen at either side of the K11 residue, consistent with other work (5), though cleavage at the N-terminal side of this residue was reported (4). Cleavage was also detected between the H18 and H19 residues of the parent Hst-5, which has previously been observed after incubation with C. albicans cells (6), but not specifically associated with Sap9.

In general, the degradation of the Hst-5 synthetic peptides with Sap9 produced results consistent with the gel electrophoresis data. For K17R and K17L, the most intense signal came from the intact peptide, as expected from the large percent of intact peptide seen in the gel electrophoresis results (FIGS. 1A-1B). Furthermore, while the parent Hst-5 was cleaved on the C-terminal side of K17, neither K17R nor K17L showed significant cleavage at this site. K11R also shows the intact peptide to be the species with the highest signal. With the exception of the peptides with K17 substitutions, the synthetic peptides with leucine substitutions showed relatively lower levels of intact peptide than the corresponding arginine-substituted peptides. Furthermore, K13L showed an apparent shift in cleavage site preference compared to the parent Hst-5. The fragments containing amino acids 1-12 and 13-24 had higher signals for K13L than the fragments containing amino acids 1-17 and 18-24, while the latter fragments had higher signals for the other modified peptides and parent Hst-5.

In contrast to incubation with Sap9, incubation of the parent Hst-5 peptide with Sap2 resulted in the intact peptide having the highest signal under the conditions tested (FIGS. 4A-4I). Although twice the concentration of enzyme was used for Sap2 compared to Sap9, the enzyme was still less effective at cutting Hst-5. This could be due to Sap2 having optimal activity at more acidic conditions than Sap9 and the slow inactivation of Sap2 that has been reported near pH 7. The lower activity of Sap2 may explain the lower number of distinct fragments detected for Hst-5 degradation by Sap2 compared to Sap9. For example, the fragments containing amino acids 1-12 and 13-24 were not significantly detected in incubation with Sap2 but were detected with Sap9. The cleavage sites that did occur with Sap2 were also observed with Sap9 and are consistent with previously reported results, except that cleavage between H18 and H19 was not previously specifically attributed to Sap2. A cleavage site at the C-terminal side of K5 (4) which was not observed here or by others also has been reported (5).

As with incubation of the parent Hst-5, incubation of the Hst-5 synthetic peptides with Sap2 resulted in higher signals for intact peptides than for proteolytic fragments. The outcome was in line with the gel electrophoresis result, which showed that, overall, the Hst-5 synthetic peptides incubated with Sap2 had more intact peptide remaining than when incubated with Sap9 (FIGS. 1A-1D). Substitutions at K17 did lead to a significant decrease in signals from fragments formed by cleavage at the C-terminal side of K17, however, unlike Sap9, Sap2 still cleaved K17L and K17R at this site.

The trends seen with the gel electrophoresis (FIGS. 1A-1D) and mass spectrometry results (FIGS. 3A-3I, 4A-4I) generally corroborate each other. Enhanced resistance to proteolysis was observed around the K17 residue for substitutions to both arginine and leucine with both Saps. The similar increase in resistance to degradation at K17, independent of the charge of the substituted residue, indicates that Sap9 and Sap2 have a preference for lysine at the K17 site and not simply a preference for a basic residue. Unlike Sap9, Sap2 still cleaved at the C-terminal side of K17, suggesting the preference is more stringent for Sap9 than Sap2. At the other locations where lysine residues were modified, Sap9 appears to favor an uncharged leucine over a positively charged arginine or lysine. The leucine residues at these sites are N- or C-terminal to an arginine in the peptide sequence, and their preference by Sap9 agrees with previous work indicating Sap9 favors cleavage of peptides that contain leucine at the N-terminal side of an arginine. Sap2, on the other hand, appears to favor lysine at the residues of Hst-5 that were studied. The preference is residue-dependent rather than charge-dependent, as Sap2 preferred lysine over both arginine and leucine. The one exception was at the K13 site, where Sap2 appears to prefer an arginine. Collectively, these results confirm gel electrophoresis results and indicate single amino-acid modifications can affect overall susceptibility to cleavage and significantly reduce cleavage at the modification site.

Example 4

Antifungal Activity of Peptides
Most Residue Substitutions do not Diminish Antifungal Activity Some previously reported modifications to Hst-5 had a negative impact on the peptide's antifungal activity (7-9). To ensure that modification of lysine and glutamic acid residues does not adversely affect the antifungal activity, we performed an antifungal activity assay to determine the reduction in the viability of C. albicans cells after exposure to the parent Hst-5 peptide and the Hst-5 synthetic peptides. Serially diluted peptides were incubated with C. albicans cells at $2.5 \times 10^5$ cells mL$^{-1}$ or $2.5 \times 10^7$ cells mL$^{-1}$ C. albicans for 30 min at 30° C. in 1 mM NaPB. The mixtures were then diluted, transferred to yeast extract peptone dextrose (YPD) media, and incubated overnight to determine the reduction in cell viability due to incubation with the synthetic peptides.

Figure 5A:
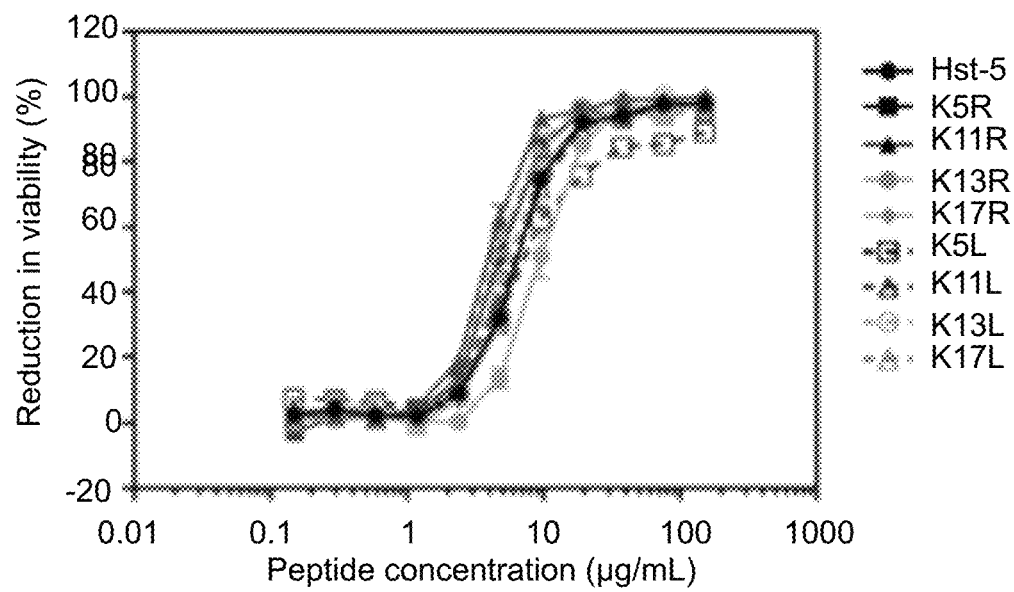
FIG. 5A-5C show antifungal activity of parent Hst-5 and the Hst-5 substituted peptides. Serially diluted peptides with lysine substituted with arginine or leucine were incubated with 2.5×10$^5$ cells mL$^{-1}$ (FIG. 5A), 2.5×10$^7$ cells mL$^{-1}$ (FIG. 5B) *C. albicans* for 30 min at 30° C. or glutamic acid substituted with arginine or leucine peptides and lysine substituted with 2 arginines peptides were incubated with *C. albicans* (FIG. 5C). Error bars represent standard error of the mean (n=6). MIC$_{50}$ values for the peptides are provided.

When incubated with C. albicans at $2.5 \times 10^5$ cells mL$^{-1}$, most Hst-5 synthetic peptides showed a trend similar to parent Hst-5, with an increasing reduction in viability with increasing peptide concentration (FIG. 5A). Hst-5 had a minimum inhibitory concentration for 50% inhibition of growth (MIC$_{50}$)) of 3.13 μM, and the MIC$_{50}$ values for the Hst-5 synthetic peptides were within one dilution factor of Hst-5. The similar growth inhibition curves and MIC$_{50}$ values (Table 2) show that the antifungal activity of Hst-5 is tolerant to substitutions of its lysine residues.

TABLE 2

Antifungal activity of synthetic peptides

| Incubated with $2.5 \times 10^5$ C. albicans cells | | Incubated with $2.5 \times 10^7$ C. albicans cells | |
| --- | --- | --- | --- |
| Peptide | MIC50 (μM) | Peptide | MIC50 (μM) |
| Hst-5 | 3.13 | Hst-5 | 50 |
| K5R | 1.56 | K5R | 50 |
| K11R | 1.56 | K11R | 25 |
| K13R | 3.13 | K13R | 100 |
| K17R | 3.13 | K17R | 100 |
| K5L | 3.13 | K5L | 100 |
| K11L | 3.13 | K11L | 50 |
| K13L | 1.56 | K13L | 50 |
| K17L | 3.13 | K17L | 100 |

Figure 5B:
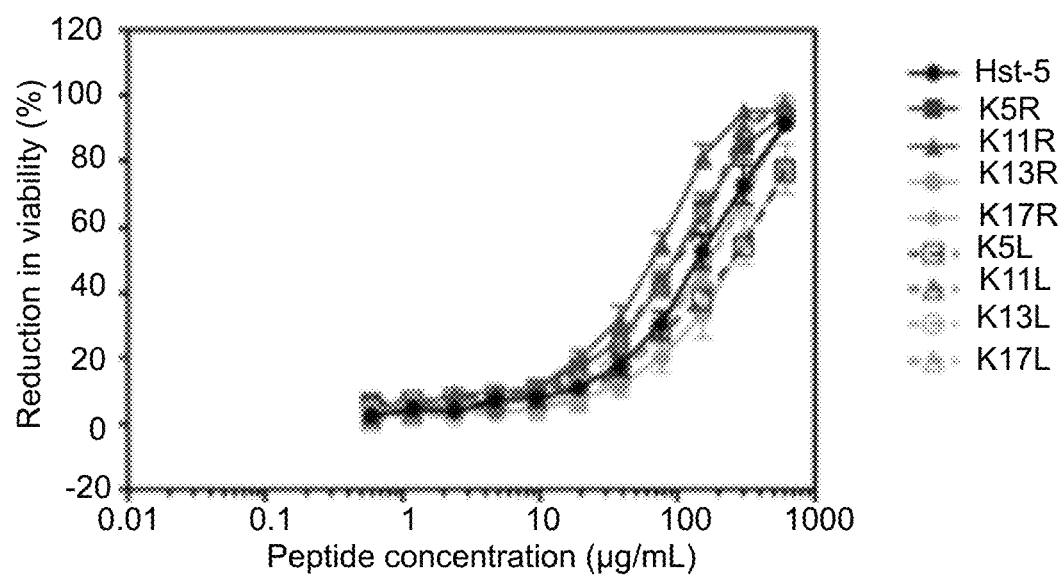
Figure 5C:
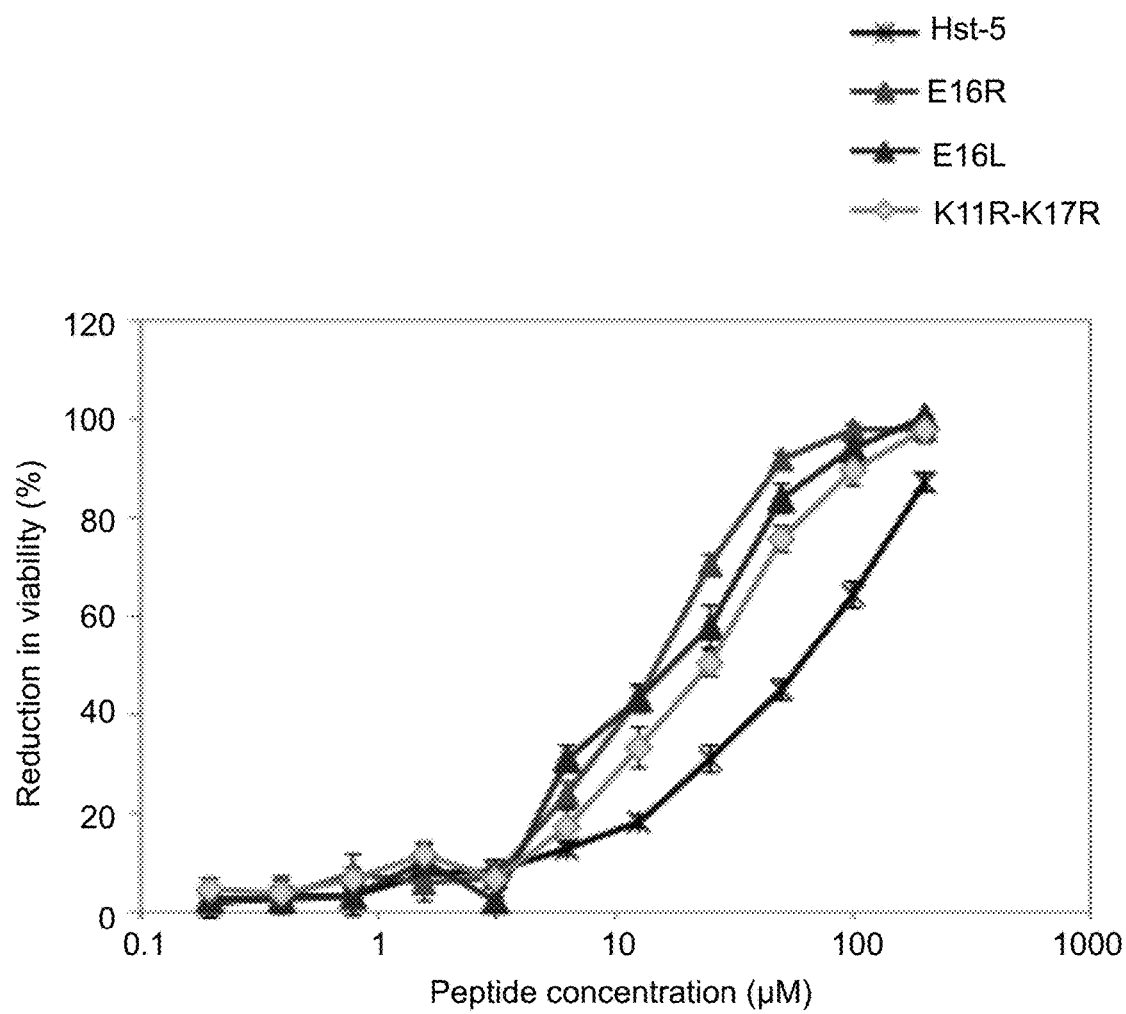
Figure 6A:
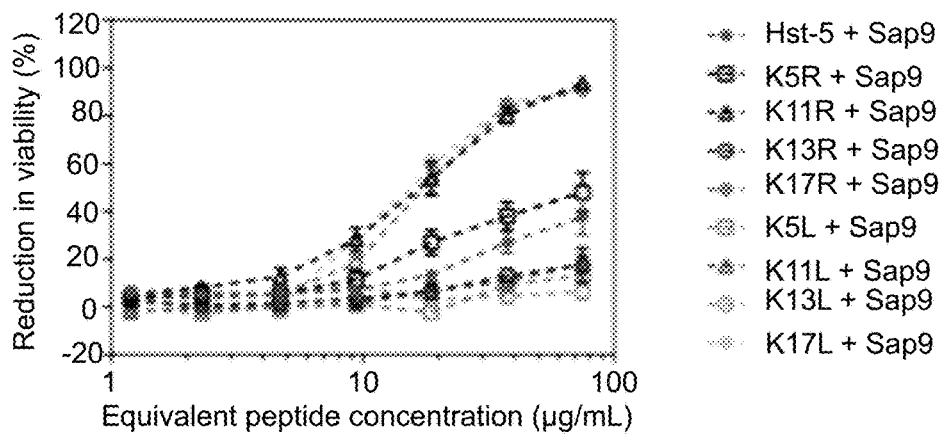
FIGS. 6A-6F show antifungal activity of parent Hst-5 and the Hst-5 synthetic peptides following incubation with Sap 9 and Sap2. The peptides (150 μg mL$^{-1}$) with Sap9 (6.25 μg mL$^{-1}$) (FIGS. 6A-6C) and Sap2 (18 μg mL$^{-1}$) (FIGS. 6D-6F) were incubated for 2 h at 37° C. Samples were serially diluted and incubated with 2.5×10$^5$ cells mL$^{-1}$ *C. albicans* for 30 min at 30° C. Error bars represent standard error of the mean (n=6).
Figure 6B:
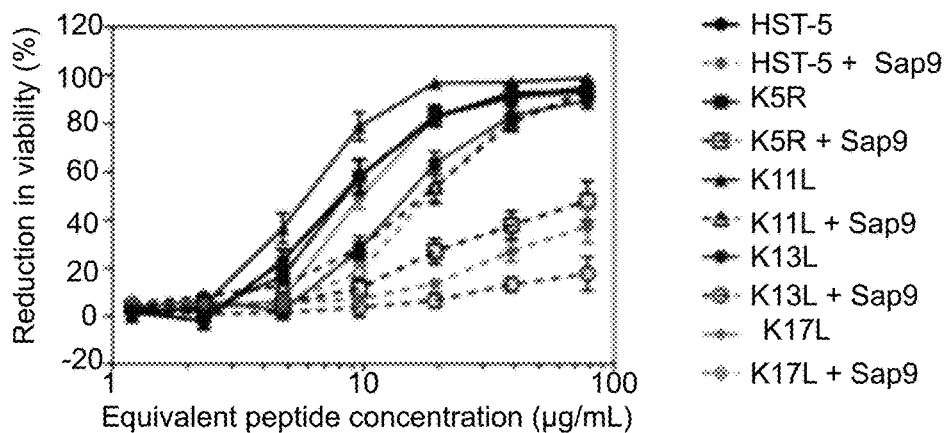
Figure 6C:
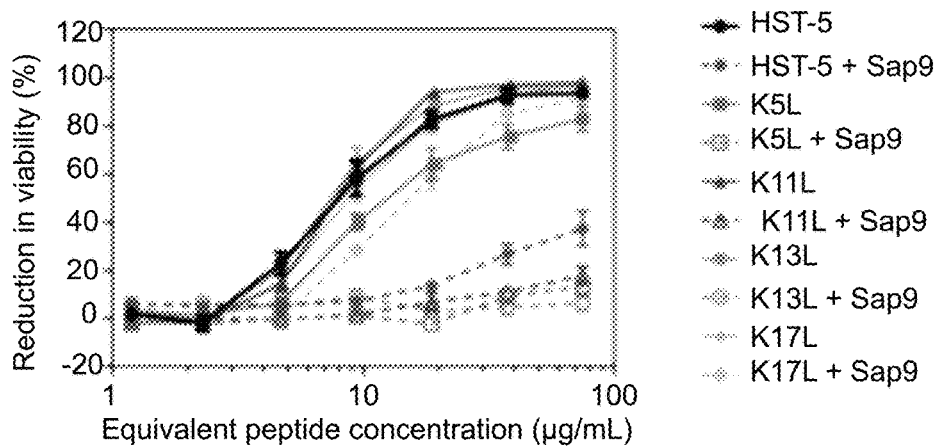
Figure 6D:
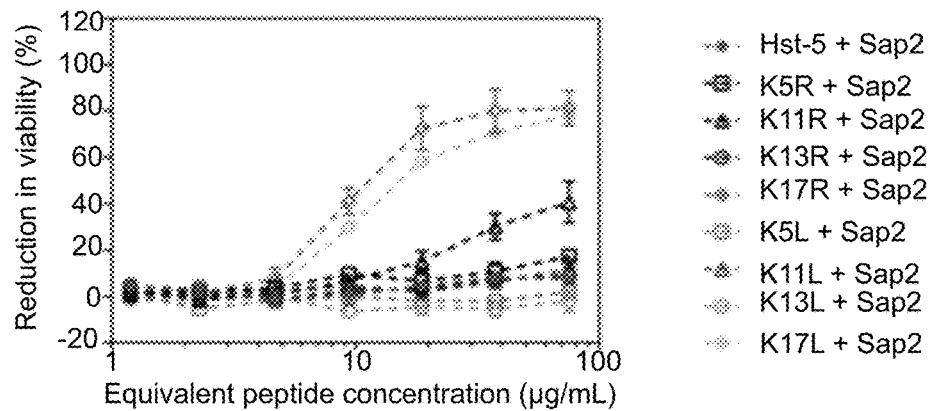
Figure 6E:
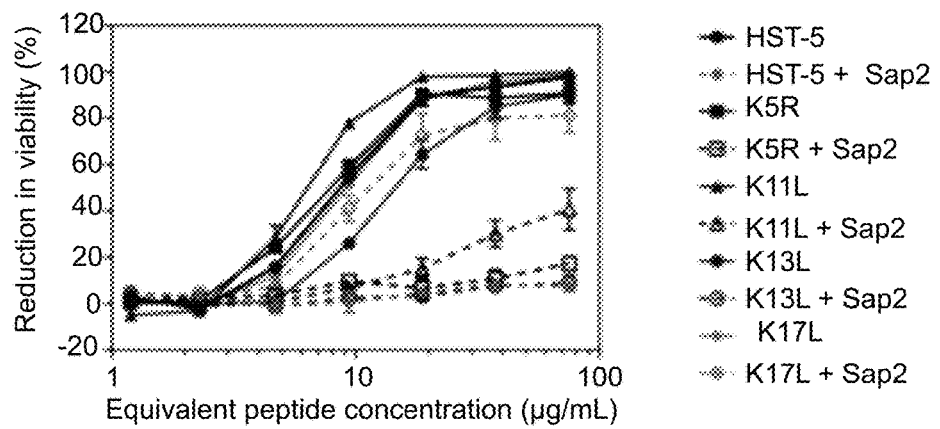
Figure 6F:
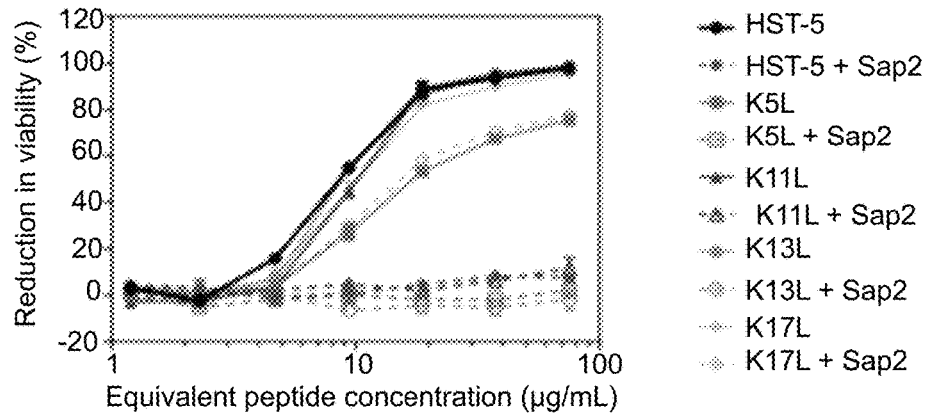
Figure 7A:
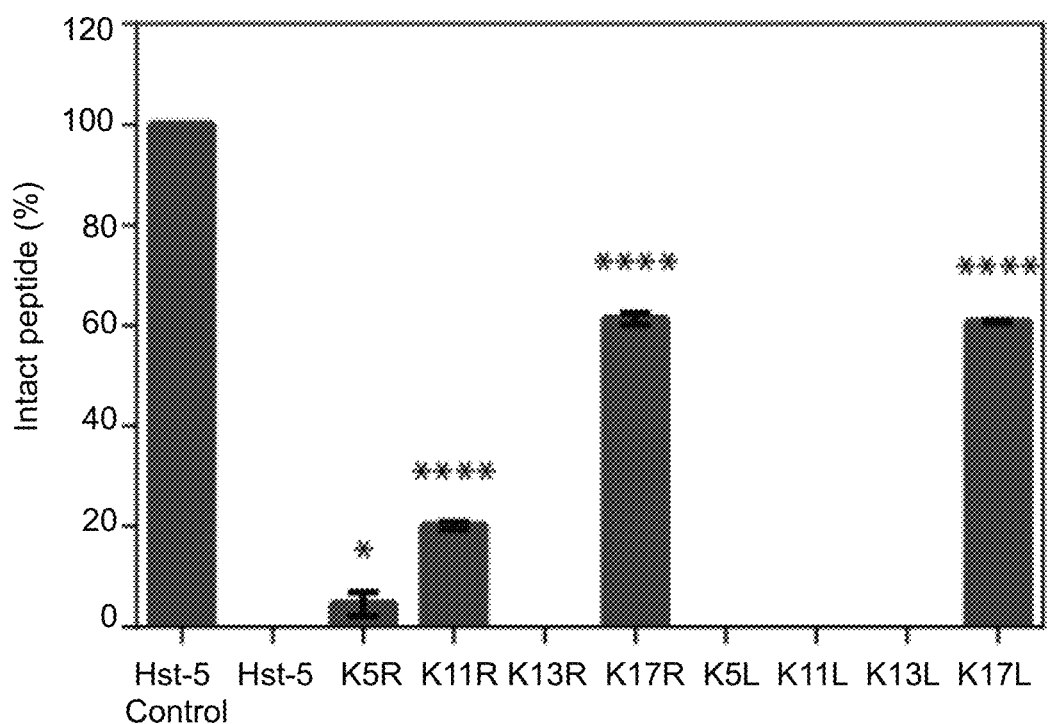
FIGS. 7A-7D show the degradation of parent Hst-5 and Hst-5 synthetic peptides by purified Sap9 (FIG. 7A) and Sap2 (FIG. 7C). The peptides (150 μg mL$^{-1}$) and Saps (6.25 μg mL$^{-1}$ Sap9 and 18 μg mL$^{-1}$ Sap2) were incubated for 2 h at 37° C. in 1 mM sodium phosphate buffer (NaPB). Samples were run on a gel (FIGS. 7B, 7D) to separate the intact peptide and peptide fragments. The amount of intact peptide was quantified by densitometry to compare the amount of intact peptide (upper band) to the peptide fragments. Error bars represent standard error of the mean (n=3). The number of asterisks indicates the level of statistical significance against parent Hst-5 incubated with the Saps: * for $p<0.05$,  for $p<0.01$, * for $p<0.001$, and **** for $p<0.0001$. The lower band in the Hst-5 control lane in FIGS. 7B and 7D is due to Coomassie dye.
Figure 7B:
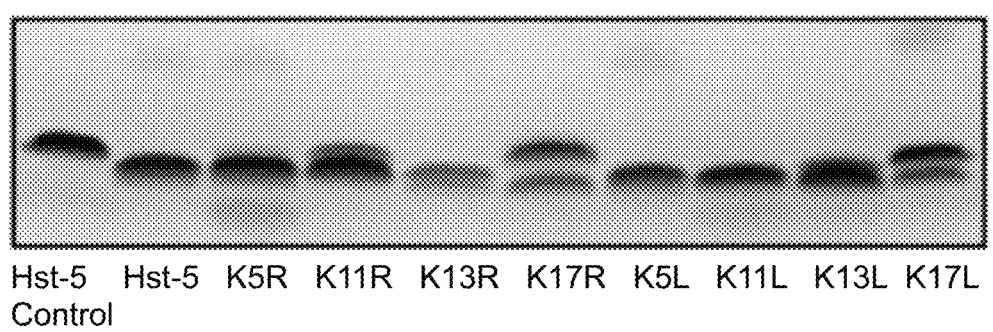
Figure 7C:
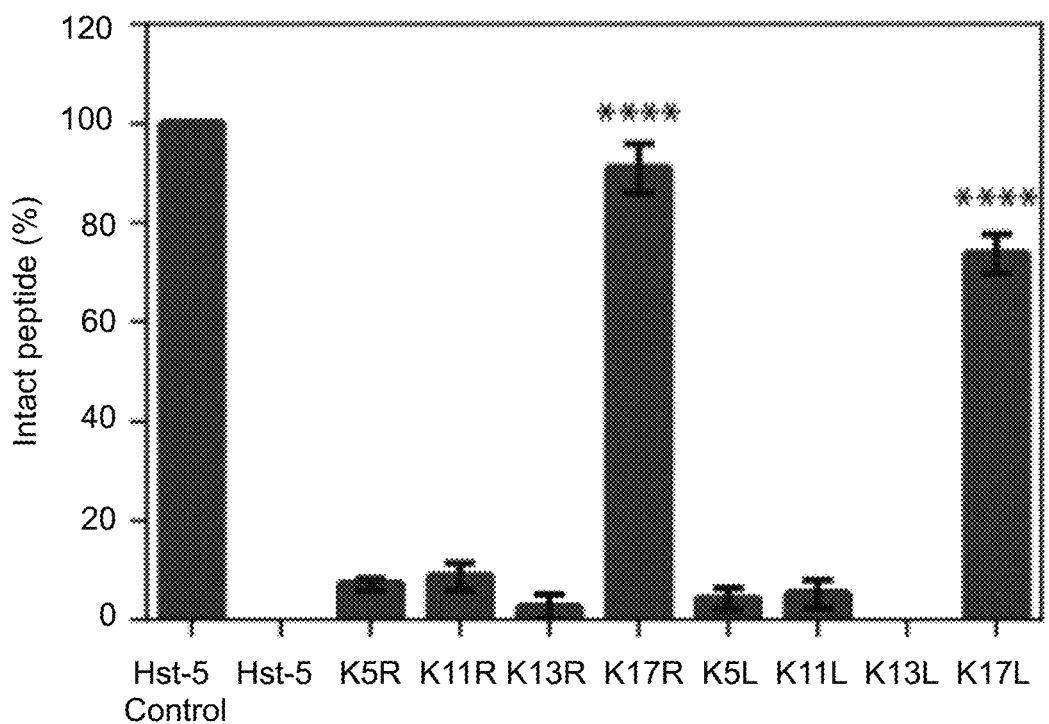
Figure 7D:
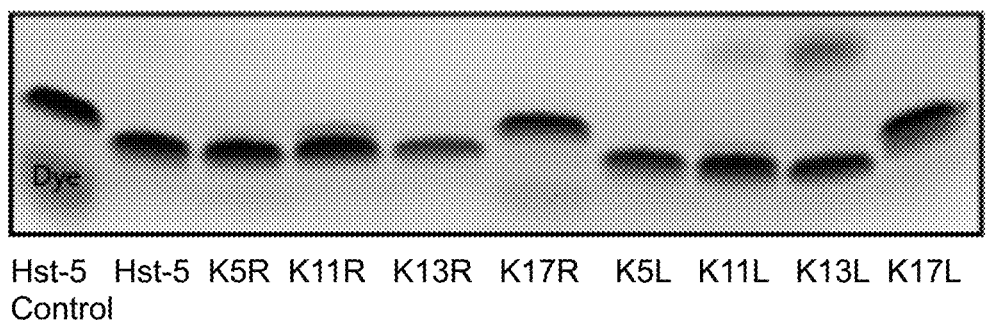

Increasing the cell concentration to $2.5 \times 10^7$ cells mL$^{-1}$ resulted in a shift of the MIC$_{50}$ value for Hst-5 to 50 μM (FIG. 5B), which is not surprising with the hundred-fold increase in cell density. With this higher cell density, the growth inhibition curves for each peptide were more widely separated, allowing differences between the antifungal activities of the peptides to be more apparent (FIG. 5B). The K11R curve showed enhanced antifungal activity that was not apparent at the lower cell concentration. Interestingly, neither K17R nor K17L showed improvement in antifungal activity despite the gel and mass spectrometry results that demonstrated more intact peptide. Moreover, the K11R-K17R, E16R, and E16L peptides all have improved in vitro antifungal activity against Candida albicans compared to Hst-5 (FIG. 5C). The improvement is greater than that for the arginine or leucine substituted peptides of SEQ ID NOS: 2-9.

Overall, the antifungal activity assay demonstrates that replacement of a lysine or glutamic acid with an arginine and/or a leucine does not abolish the antifungal activity of the Hst-5 and may lead to improvements. While there have been no previous studies evaluating the effect of lysine to arginine modifications on the antifungal activity of Hst-5, it was reported that a lysine to leucine substitution in a fragment of Hst-5 called dh-5 showed similar activity to the peptide containing lysine, further supporting the tolerance of Hst-5 to lysine-to-leucine modifications.
Several Hst-5 Synthetic Peptides Retain Antifungal Activity after Treatment with Saps After confirming that substitutions to the lysine residues did not eliminate antifungal activity, whether the peptides retained their antifungal activity after exposure to purified Saps was shown. To amplify differences in antifungal activity due to degradation by the Saps, the concentrations of the Saps was increased by at least two-fold compared to the concentrations used for the gel electrophoresis data in FIGS. 1A-1D (to 6.25 μg mL$^{-1}$ for Sap9 and 18 μg mL$^{-1}$ for Sap2).

Incubation with Sap9 led Hst-5 to lose over 60% of its antifungal activity, while incubation with Sap2 almost completely eliminated its activity (FIGS. 6A-6F). On the other hand, both K17 synthetic peptides retained much of their antifungal activity after exposure to each Sap, which is consistent with the high level of intact peptide that remained following incubation with both Sap9 (over 60% remaining for each peptide) and Sap2 (over 90% remaining for K17R and over 70% remaining for K17L). The K11R peptide also had a strong performance in the antifungal activity assay following exposure to Sap9, with a level of activity similar to that of the K17 synthetic peptides. Following degradation by each of the Saps, the arginine-substituted peptides retained more antifungal activity compared to the analogous leucine-substituted peptides; for example, the Sap9- and Sap2-degraded K5R and K11R synthetic peptides still displayed some antifungal activity, while the degraded K5L and K11L synthetic peptides showed almost none.

The K5R and K11R synthetic peptides that retained some antifungal activity following degradation also retained some intact peptide after Sap9 incubation (4.5% and 20%, respectively), while no statistically significant amount of these peptides remained after Sap2 incubation. The presence of intact K5R and K11R but not intact K5L and K11L after incubation at the higher Sap9 concentration further supports a preference for leucine at these sites by Sap9 and also shows a preference for lysine over arginine, since the parent Hst-5 is completely degraded under these conditions.

Although the synthetic peptides with the largest amount of intact peptide remaining had the strongest antifungal activity, intact peptide was not required for antifungal activity. The parent Hst-5 peptide had no intact peptide remaining after incubation with Sap9, but it did show a measurable level of antifungal activity. Similarly, no statistically significant amount of intact K11R remained after incubation with Sap2, but this peptide also exhibited antifungal activity. These results indicate that the antifungal activity comes not only from the intact peptide but also from the degradation fragments, which is consistent with earlier work that identified only amino acids 4-15 of Hst-5 as critical for antifungal activity. Additionally, the present invention indicates that, while some peptide modifications make the intact peptide more robust (e.g., K17R, K17L), others can lead to degradation fragments with improved antifungal activity compared to the degradation fragments of parent Hst-5 (e.g., K11R).

K11R Peptide

Figure 3A:
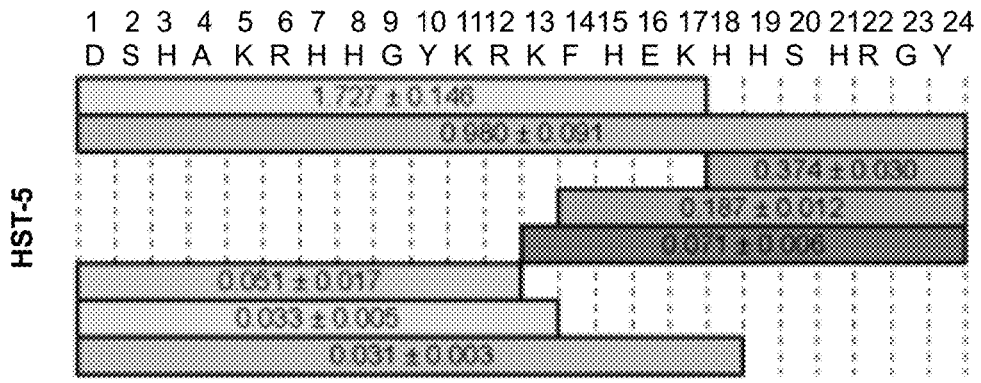
FIGS. 3A-3I show relative mass spectrometry signal intensity of intact peptide (gray) and peptide fragments produced by incubation of parent Hst-5 and Hst-5 synthetic peptides (modified residue in red) with 3.13 μg mL$^{-1}$ Sap9. The values on each fragment indicate the signal for the fragment relative to the signal for an internal standard. Fragments with signals greater than 0.01 relative to the standard are shown. The relative signal is the mean with standard error (n=3).
Figure 3B:
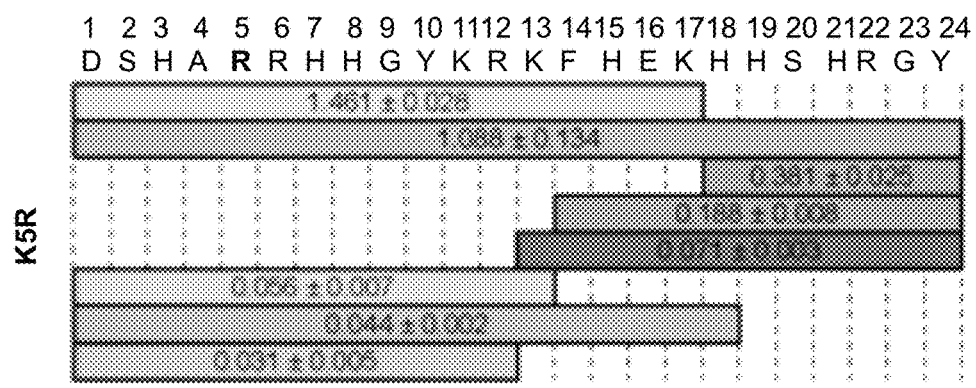
Figure 3C:
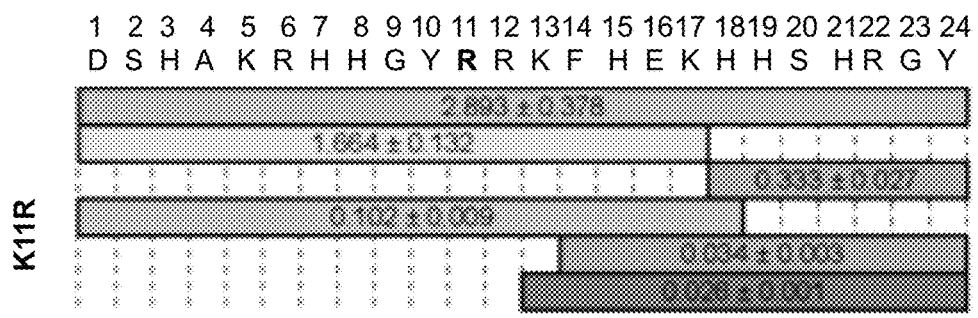
Figure 3D:
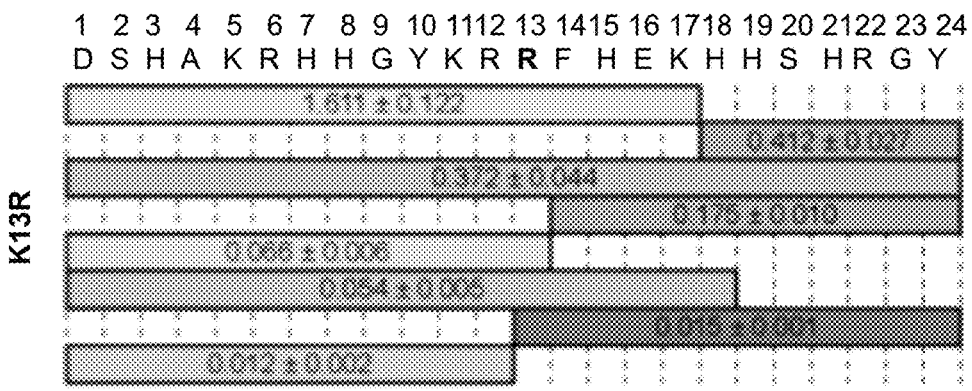
Figure 3E:
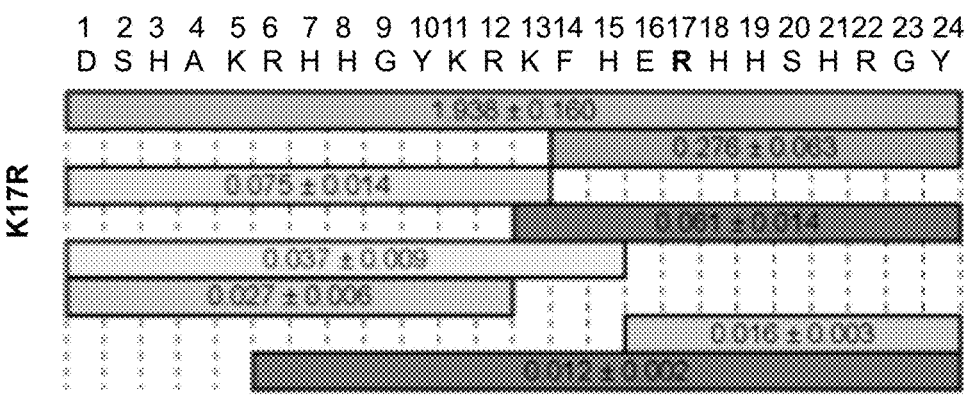
Figure 3F:
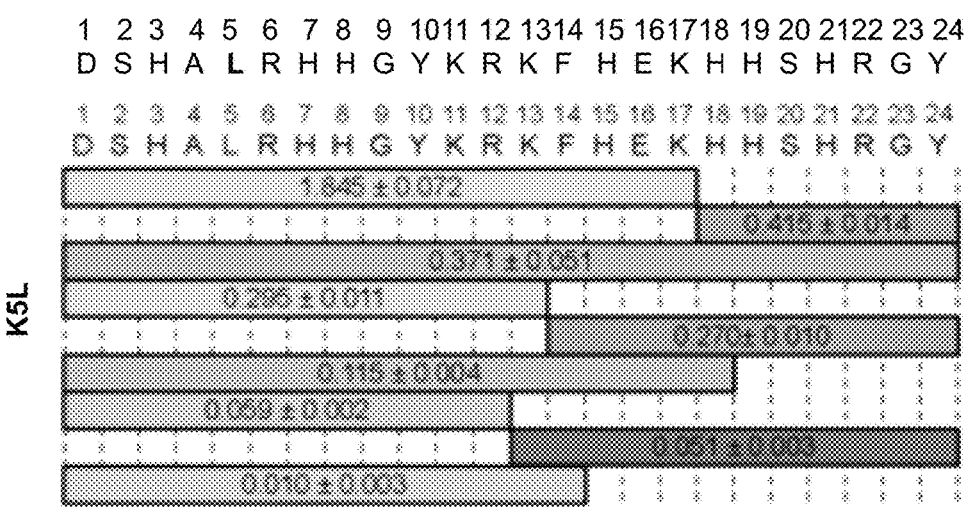
Figure 3G:
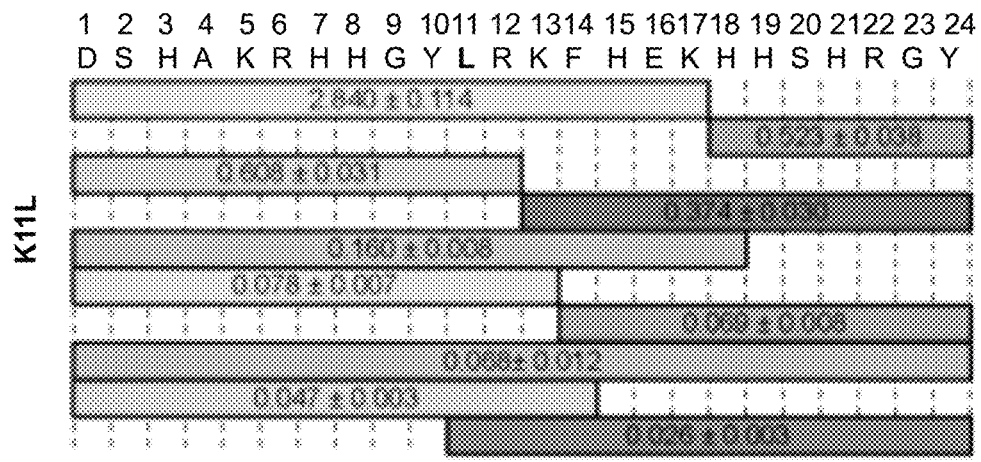
Figure 3H:
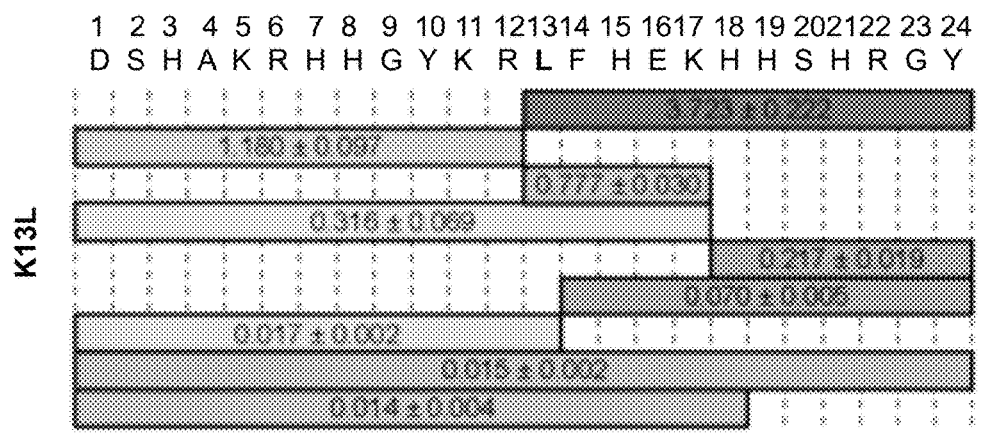
Figure 3I:
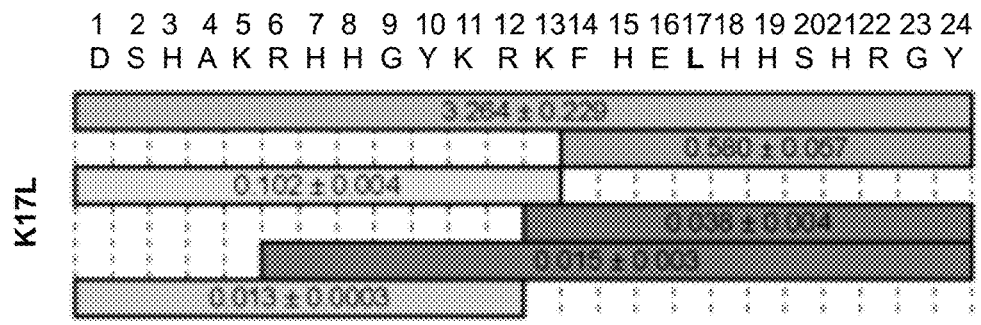
Figure 4A:
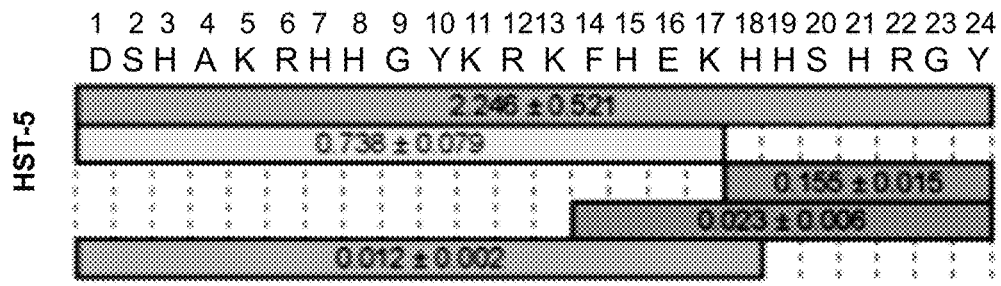
FIGS. 4A-4I show relative mass spectrometry signal intensity of intact peptide (gray) and peptide fragments produced by incubation of parent Hst-5 and Hst-5 synthetic peptides (modified residue in red) with 6.25 μg mL$^{-1}$ Sap2. The values on each fragment indicate the signal for the fragment relative to the signal for an internal standard. Fragments with signals greater than 0.01 relative to the standard are shown. The relative signal is the mean with standard error (n=3).
Figure 4B:
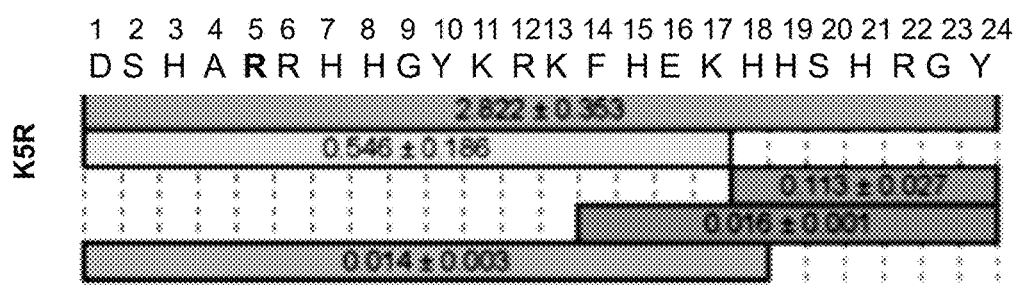
Figure 4C:
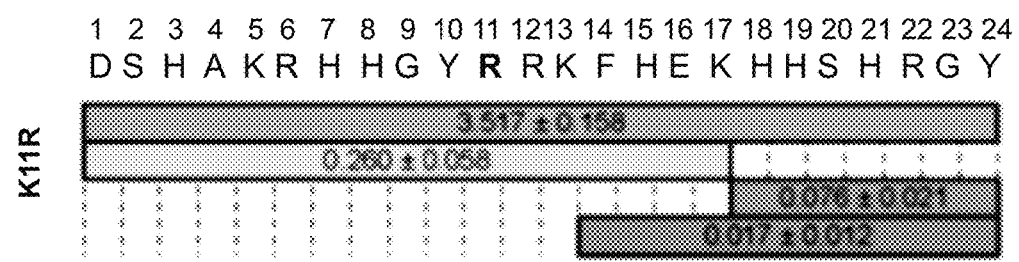
Figure 4D:
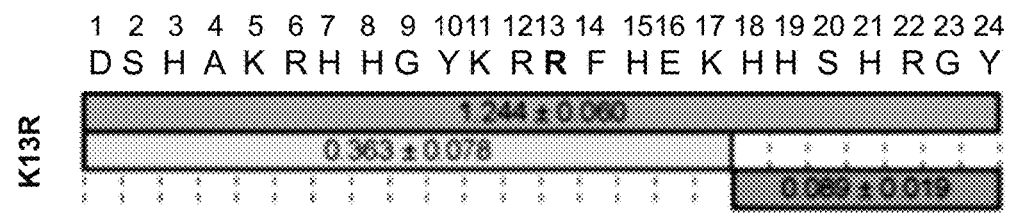
Figure 4E:
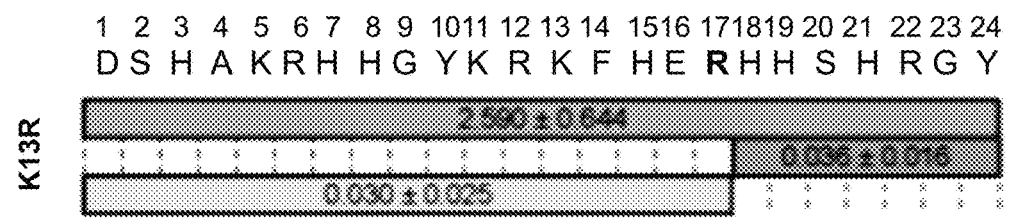
Figure 4F:
Figure 4G:
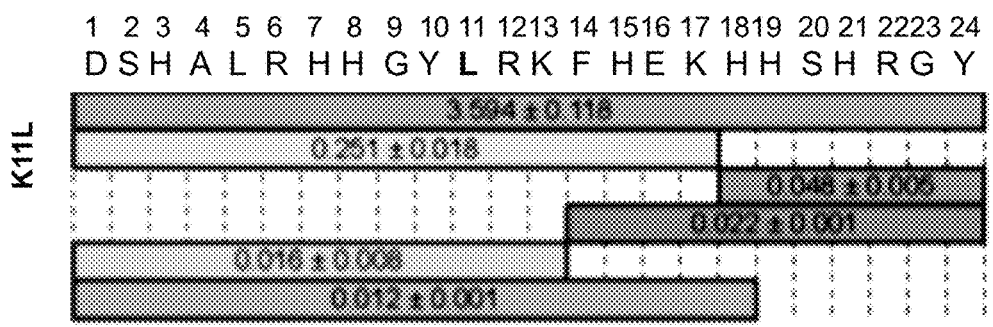
Figure 4H:
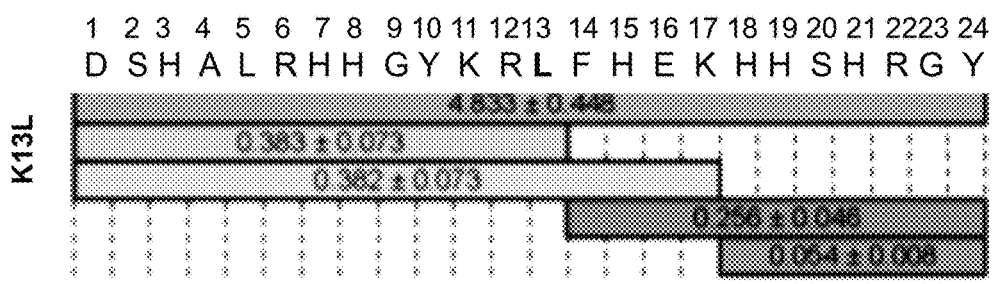
Figure 4I:

The K11R peptide showed interesting results in the assays. In the antifungal activity assay with $2.5 \times 10^7$ cells/mL, K11R showed improvement in antifungal activity compared to Hst-5 (FIG. 5B). At a concentration of 50 µM, K11R had significantly higher antifungal activity than Hst-5. This result was unexpected as the gel electrophoresis of the peptide incubated with even higher cell concentration of $1 \times 10^9$ cells/mL (FIGS. 2A-2B) did not show a significant difference in degradation of the peptide compared to Hst-5. While incubation of K11R with the lower Sap9 concentration did not show a significant increase in resistance to the protease (FIGS. 1A-1B), the mass spectrometry analysis showed a higher abundance of intact peptide than fragments (FIG. 3D). Incubation of this peptide with the higher Sap9 concentration showed a significant reduction in degradation compared to Hst-5 (FIGS. 7A-7D), and substantial antifungal activity was retained by the degraded peptide (FIGS. 6A-6F). These improvements in proteolytic resistance and antifungal activity were observed even though no cleavage was observed on either side of K11 in the mass spectrometry analysis of Hst-5 (FIG. 3D). The results with K11R further support that residue modification affects not only cleavage at the site of the modification but cleavage of the substrate as a whole. It also shows the need to evaluate peptide modifications with multiple assays to fully characterize the effect of the modifications.

Example 5

Hydrogel Formulation

The bioadhesive hydrogel formulation was prepared and evaluated as previously described (1). Briefly, hydroxypropyl methylcellulose (HPMC) K100 Premium LV (Dow Chemical, Midland, Mich.; donated by Colorcon Inc.) is a hydrophilic gelling polymer commonly used in FDA-approved formulations. Specifically, HPMC is widely used in the pharmaceutical industry for controlled release of drugs. HPMC grade K100 was selected due to its medium-length chain. Several concentrations of the polymer were evaluated for suitability as delivery system for the peptides. Based on viscosity, stability and rate of diffusion of peptide at various physiologically relevant temperatures, it was determined that 4% was the optimal concentration for use in animals. However, for human application, it is likely that a more viscous formula may be more suitable; in that case the formulation can be made at higher concentrations. An aqueous solution of Hst-5 was prepared by dissolving the peptide in 1 mM PBS, and HPMC was added to the solution at 4% wt/wt, and was mixed until a clear gel solution formed. Hst-5 was incorporated at a final concentration of 2 mg/ml. Gels were stored at 4° C. and tested regularly for stability. Vehicle polymer with no Hst-5 incorporated was used as negative control in all experiments.

Example 6

In Vivo Assessment of Gel Formulations: Animals
General

All animal studies are performed at the AAALAC Certified Animal Facilities of the University of Maryland, Dental School, Baltimore and all animal studies were approved by IACUC (Animal protocols #0416013 and #0416014). Healthy pathogen-free age-matched (6-8 weeks) female and male C57BL/6J mice (oral candidiasis model) and BALB/cJ (wound healing model) and Sprague-Dawley male and female rats (denture stomatitis model) standard strains are used. The rodent models are approved by IACUC and established. Animals are randomly divided into groups with 5 mice in each group and all studies are performed on 3 separate occasions for statistically significant data. Animals are housed at a maximum of 5 per cage for mice or 2 per cage for rats and throughout the experimental period, animals are fed a standard diet and given water ad libitum. Rats for the denture stomatitis model are fed liquid diet.

Animals are monitored daily for signs of distress including hunched posture, lethargy, loss of food or water consumption, alopecia over 25% of the body surface, or diarrhea lasting 2-3 days. Oral tissue is inspected daily and distress to the animals assessed. Animals are monitored for any signs of hydration and their weight assessed to ensure proper eating. As per IACUC guidelines, animals are euthanized if they lose more than 20% of their body weight. The help of the attending veterinarian will be sought if such severe signs of disease manifest and appropriate action taken to euthanize these animals. Upon completion of the infection and treatment protocols, animals are euthanized via $CO_2$ inhalation followed by cervical dislocation as a secondary method. Immediately following euthanasia, oral tissue is harvested for analysis. While under anesthesia, animals are placed on heating pads maintained at 37° C.

Mouse Model of Oral Candidiasis (OC)

Following anesthesia, calcium alginate swabs saturated for 5 minutes with *C. albicans* cell suspension (1×106 cells/ml) are placed under the tongues of the C57BL/6J mice for 60 minutes. Experimental animals will receive daily topical gel applications. Development of oral candidiasis between treated and untreated control group will be assessed based on clinical picture (white lesions on tongues and oral tissue) as well as level of microbial recovery from harvested tongues.

Rat Model of Denture Stomatitis

In this model, an appliance fabricated of denture acrylic is fitted on the rat palate and is secured by orthodontic wires. The denture material and associated palatal tissue is infected with *C. albcians* cell suspension. Experimental animals receive topical gel applications to the appliance and infected tissue and development and progression of denture stomatitis and tissue inflammation is comparatively monitored over time between treated and untreated control group. Efficacy of gel to prevent biofilm formation on denture material and tissue infection is evaluated by processing harvested appliance and infected tissue for microbial recovery and microscopic examination.

Rodent Model of Dental Caries

In this model, rodents (mice or rats) are infected with the cariogenic bacterial pathogen *Streptococcus mutans* directly or through drinking water. Experimental animals receive topical gel applications to the tongues and teeth. Tissue and teeth are harvested at different time points and processed to comparatively assess microbial recovery from oral cavity between treated and untreated control group. Rats are evaluated for development of carious lesions on teeth.

Rodent Ligature Model of Periodontitis

The rodent (mice or rats) liguature model is a standard model of periodontitis. Gingival wounds are induced by tying a thread around the tooth surface at the gum level. The ligature model is a standard model for longitudinal infection studies. Ligatures are not invasive and animals tolerate it well and its presence does not affect their ability to eat or drink. To induce periodontitis, C57BL/6J mice are sedated and a sterilized 5-0 silk thread ligature is used (Roboz Surgical Instrument Co., MD, USA). Ligatures are soaked in suspensions of vehicle, *Porphyromonas gingivalis* (Pg), *Fusobacterium nucleatum* (Fn) or in combination are subgingivally tied around maxillary molars. Sutures are tied gently to prevent damage to the periodontal tissue. The ligatures remain in place in mice throughout the experimental period and are inspected daily and are repositioned, if necessary, to maintain the ligature during the entire experimental period.

Mouse Model of Oral Wound-Healing

The mouse oral-wound healing model is a standard model of lingual surface wounds. A standard mouse oral woundhealing model is used where lingual surface wounds are inflicted by punch biopsies of tongues. Briefly, superficial circular punch biopsy wounds measuring ~2.0 mm are made in the middle of the tongue of C57BL/6J mice using a 1.00 mm Biopsy Punch (Acu-punch, Ft. Lauderdale, Fla.) by ablating the epithelial layer without damage to the underlying muscle.

Example 7

In Vivo Assessment of Gel Formulations: Methods and Materials

Bacterial Strains and Growth Conditions

*Porphyromonas gingivalis* (Pg, strain ATCC 33277) and *Fusobacterium nucleatum* (Fn, ATCC 25586) strains are maintained on anaerobic blood agar plates supplemented with required nutritional needs in an anaerobic chamber containing 90% N2 and 10% CO2 at 37° C. for 10 days. For experiments, organisms are grown anaerobically in Trypticase soy broth (TSB) containing 1% yeast extract, 5 μg/ml hemin, and 2.5 μg/ml menadione. Bacterial cell densities are adjusted using a spectrophotometer. Following incubation at 37° C. for 5 days, bacteria are harvested and are washed with sterile phosphate-buffered saline (PBS). *Porphyromonas gingivalis* or *Fusobacterium nucleatum* is resuspended at a final cell density of $1 \times 10^9$ cells/ml in PBS and is mixed thoroughly with an equal volume of sterile 2% (wt/vol) low-viscosity carboxymethyl cellulose (CMC) as the vehicle.

Assessment of *C. albicans* Recovery from Infected Tissue

Tongues are harvested, weighed and cut in half. One half is homogenized and tissue homogenates are diluted and are cultured on Yeast Peptone Dextrose (YPD) agar media as previously described (1). Plates are incubated at 37° C. for 48 hours and colonies are enumerated and expressed as colony forming units (CFUs). Gingival tissue is homogenized and plated on appropriate media and incubated in an anaerobic chamber as described in bacterial strains and growth conditions. Microbial burden is determined based on tissue weight and expressed as CFUs/gram tissue.

Tissue Histopathology Analyses: Fungal Infection

In order to visually assess fungal presence and tissue invasion, one half of the tongues are processed for histopathology and microscopic analysis as previously described (1). Tissue is fixed in paraformaldehyde, embedded in paraffin and sectioned and sections are deparaffinized with xylene and stained with PAS. The whole periphery of each infected tongue section is examined by light microscopy and comparatively evaluated based on the presence and extent of adhering fungal cells and penetration of the epithelium by invasive hyphae. Tissue sections also are comparatively evaluated for markers of inflammation and influx of immune cells in addition to fungal presence.

Tissue Histopathology Analyses: Inflammation

The samples for histologic analysis are embedded in paraffin and serial sections of 4-mm thickness are obtained and are mounted on slides, and are stained with hematoxylin and eosin (H&E). Using an optical microscope the inflammatory reactions of the connective tissue and periodontal ligament present in the palatal area are blindly examined and the inflammatory reactions of the connective tissue are assesed. The histologic analysis includes the area corresponding to the periodontal tissues in the palatal side of the molar palatal root. The severity of the inflammatory process is classified in each region using polymorphonuclear leukocyte and mononuclear cell inflammation scoring and ranked as follows: 0=no inflammatory cells; 1=mild inflammation (a some inflammatory cells); 2=moderate inflammation (remarkable inflammatory cells); or 3=severe inflammation (predominance of inflammatory cells).

Tissue Histopathology Analyses: Wound Healing

At the end of a treatment period, tissues from the wounded area are collected and are processed for histopathology analysis. Samples are fixed in 4% paraformaldehyde, then bisected and embedded in paraffin. Serial sections from the central portion of the wound are stained with hematoxylin and eosin, and the extent of wound closure between the groups is comparatively determined. A wound is defined as completely healed/closed when all central serial sections demonstrated an intact superficial epithelial layer over the wound area.

Serial sections from the central wound area are used for analysis. Samples are processed as described herein. Markers for neutrophils (Ly6G) and macrophages (CD68) as indicators of inflammation, and CD31 (marker for angiogenesis) and Factor VIII antigen (measurement of vascular density for localization of angiogenesis) are used. For visualization, the Vector NovaRed Substrate Kit is used and sections are counterstained with hematoxylin. The slides are scanned using Aperio Scanner and digital slides are analyzed. For each specimen, equivalent fields are examined on serial sections to enable comparisons to be made between markers and localization is assessed both qualitatively and quantitatively. The number of neutrophils and macrophages are calculated as number of positive cells counted in 10 high-power fields divided by 10. CD31 positive areas within the wound bed and the percent vascularization are calculated as: % CD31+ve area=(CD31+ve area/Total wound bed area)×100. The area of Factor VIII staining will be calculated as % Factor VIII (Angiogenesis)=(Factor VIII+ve area/Total wound bed area)×100.

Cytokine Measurement

For cytokine measurements, tissue is homogenized with a protease inhibitor cocktail. Homogenates are centrifuged at 12,000 rpm for 10 min at 4° C. and supernatant is collected and is stored at −80° C. until further use for ELISA testing. Multiplex cytokine analysis is performed on the homogenates at the Univ of Maryland, Baltimore Cytokine Core (www.cytokines.com/luminex-multianalyte.php) using the Luminex Multianalyte System. Data are calculated using BioRad's BioPlex Software. Each sample is measured in duplicate and the results expressed in pg/ml.

Quantitative Analyses of mRNA Expression (qRT-PCR)

Total RNA is extracted from gingival tissues between the molars using TRIzol reagent (Sigma). 400 ng total RNA is reverse transcribed using a SuperScript II reverse transcriptase kit (Invitrogen). Primers for glyceraldehyde-3-phosphate dehydrogenase (GAPDH), RANKL, osteoprotegerin (OPG), IL-1β, IL-10, TNF-α and other relevant genes are used and qPCR is conducted using LightCycler SYBR green I master solution and a LightCycler 480 system (Roche) according to the manufacturer's instructions. Results are represented as the mean mRNA expression from duplicate measurements normalized using the internal control GAPDH and are expressed as a fold change compared to the levels determined in cDNA samples prepared from healthy control gingival tissues.

Scanning Electron Microscopy (SEM)

For representative images, tissue is processed for SEM. Briefly, tongues are fixed in 2% paraformaldehyde/2.5% glutaraldehyde and, following washing steps with PBS, are post-fixed with 1% osmium tetroxide, then rinsed with PBS and dehydrated using a series of washes with ethyl alcohol, (30-100%). Samples are dried by critical point drying using an Autosamdri-810 (Tousimius), mounted on aluminum stubs and sputter coated with 10-20 nm of Platinum/Palladium and imaged with a Quanta 200 scanning electron microscope (FEI Co. Hillsboro).

Flow Cytometry

The nature of the cellular infiltrate in the healing wounds is assessed using flow cytometry and markers for macrophages, neutrophils and CD31 positive cells. Tissues are placed in digestion medium after being minced finely using a scalpel blade. Homogenates are filtered, the single cell suspensions are diluted and are directly stained with Ly6G-specific antibody, Gr-1 (RB6-8C5), or F4/80 antibodies. Samples are analyzed at the UMB Flow Cytometry Core at www.umgcc.org/research/flow_cytometry.htm.

Example 8

In Vivo Assessment of Gel Formulations: Treatment and Prevention of Oral Candidiasis Infection and Treatment The mouse model of oral candidiasis is used. On the day of infection the regimen 1 group of mice receives only one gel application prior to infection and the regimen 2 group of mice receives 2 gel applications, prior to and immediately post-infection. In regimen 1 on the day of infection, gel (50 µl) is topically applied with a pipette covering the tongue and sublingual area and the oral mucosa of animals under anesthesia 15 minutes prior to sublingual infection with *C. albicans* as described (1). In regimen 2 in addition to the application prior to infection, mice similarly receive a subsequent application 15 minutes post-infection with *C. albicans*. Animals are euthanized 4 days post-infection and the tongues are clinically evaluated for signs of OC as indicated by the presence of white lesions.

Animal Groups

Ten mice are randomly included in each experimental and control groups with 10 mice in each group (40 mice per occasion). Control mice receive treatments with vehicle gel with no peptide. The groups are shown in Table 3.

TABLE 3

| Group | Mice |
|---|---|
| 1 | Control group receiving 1 application of vehicle gel |
| 2 | Experimental group receiving 1 application of peptide gel treatment |
| 3 | Control group receiving 2 applications of vehicle gel |
| 4 | Experimental group receiving 2 applications of Hst-5 gel treatment |

Example 9

In Vivo Assessment of Gel Formulations: Treatment of Oral Candidiasis with K17L and K11R Synthetic Peptides Mice were rendered susceptible to candidiasis by subcutaneous administration (0.2 ml) of cortisone acetate (200 mg/kg body weight) in the dorsum of the neck every other day starting one day before infection (total 3 injections). On day of infection, mice were anesthetized by intraperitoneal injections (0.5 ml) of Tribromoethanol (Sigma-Aldrich) (250 mg/kg body weight). While under anesthesia, animals were placed under a heating lamp maintained at 37° C. Anesthetized animals were orally infected by placing calcium alginate swabs (Fisher Scientific) saturated for 5 min with *C. albicans* ($1 \times 10^6$ cells/ml) yeast cell suspension sublingually for 50 min. Animals were placed in a supine position and monitored until they recovered from anesthesia. One day post-infection with *C. albicans*, animals were anesthesized and 100 µl of gels was applied to the oral cavity covering the whole surface and sublingual areas. Similarly, same treatment was administered on the subsequent two days for a total of 3 applications. Animals were euthanized 4 days post-infection. Tongues were harvested, weighed, homogenized and cultured in triplicate on yeast chromogenic media CHROMagar (DRG International, Inc.). Plates were incubated for 24 h at 37° C. and viable counts were enumerated and expressed as log CFUs/gram tissue.

Animal Groups

Animals were divided into 4 groups with 5 mice in each group. The groups are shown in Table 4.

TABLE 4

| Group | Mice |
|---|---|
| 1 | Control mice administered vehicle gel |
| 2 | Mice administered Hst-5 gel |
| 3 | Mice administered gel with peptide K17L |
| 4 | Mice administered gel with peptide K11R |

Figure 8:
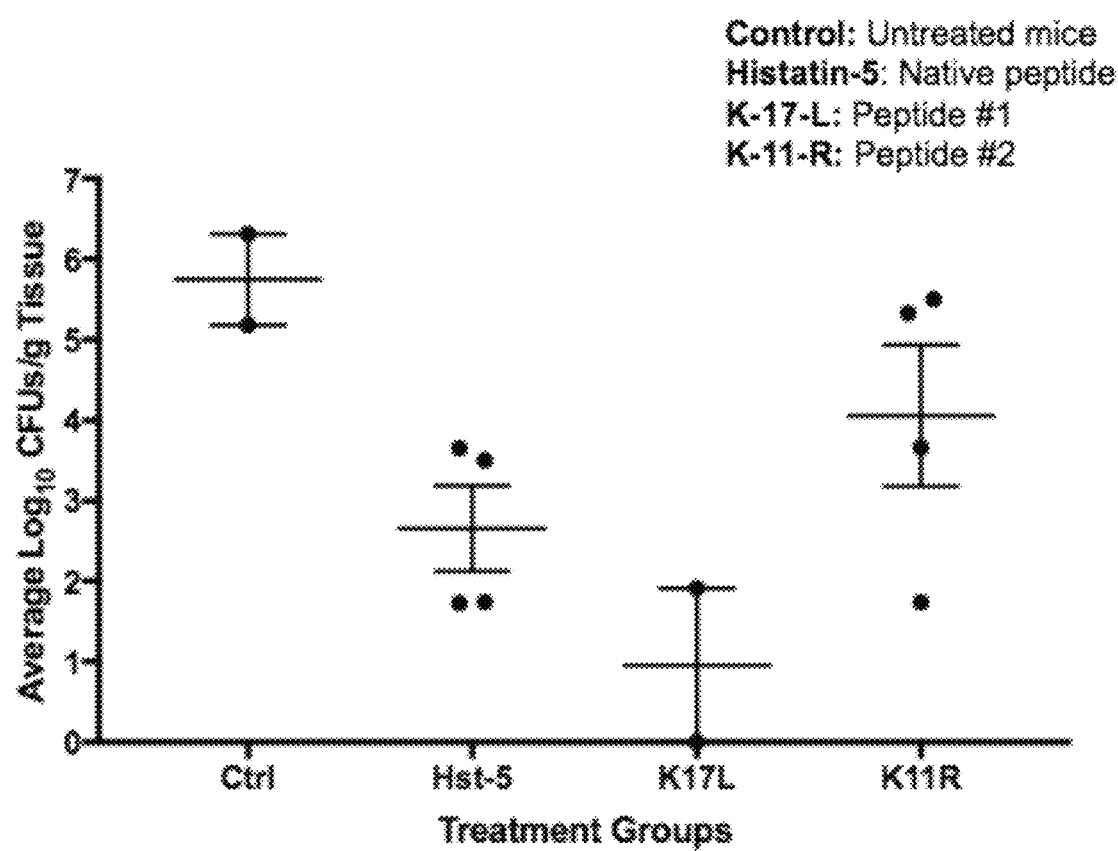
FIG. 8 shows a scatter plot representing the CFUs as cells/gram tissue recovered from each mouse in the 4 groups after 3 treatments each. The groups are control, Histatin-5, K17L peptide, and K11R peptide.

The colony forming units (CFUs) recovered per gram of tissue after treatment were counted (FIG. 8). The average CFUs were $1 \times 10^6$ cells/per gram tissue for the control, $1 \times 10^5$ cells/per gram tissue for Histatin-5, $9 \times 10^4$ cells/per gram tissue for K17L peptide, and $2 \times 10^5$ cells/per gram tissue for K11R. Results demonstrated that all infected control mice developed advanced candidiasis characterized by white lesions on the tongues and other mucosal surfaces including the pharynx. In contrast, minimal isolated lesions were seen on the tongues of all the mice receiving Hst-5 and peptide gels. The clinical picture was confirmed by tissue culturing where based on CFU counts, a significantly lower level of *C. albicans* was recovered from all the treated mice compared to control mice.

Example 10

In Vivo Assessment of Gel Formulations: Immunomodulatory and Anti-Inflammatory Properties Against Tissue Damage Associated with Oral Candidiasis Infection and Treatment The mouse model of oral candidiasis is used. Mice receive 1 to 3 gel applications and groups of mice are euthanized and tissue harvested daily. Tissue also is harvested from a group of uninfected/untreated animals for baseline values.

Animal Groups

Mice are divided randomly into 8 groups for each time point, with 5 mice in each group (40 mice per occasion).

Control/untreated mice receive vehicle gel with no peptide. The groups are shown in Table 5.

TABLE 5

| Group | MIce |
|---|---|
| 1 | Control mice uninfected (Day 0). |
| 2 | Control mice infected untreated euthanized on Day 2 |
| 3 | Mice with 1 treatment euthanized on Day 3 |
| 4 | Control mice untreated euthanized on Day 3 |
| 5 | Mice with 2 treatments euthanized on Day 4 |
| 6 | Control mice untreated euthanized on Day 4 |
| 7 | Mice with 3 treatments euthanized on Day 5 |
| 8 | Control mice untreated euthanized on Day 5 |

Example 11

In Vivo Assessment of Gel Formulations: Antibacterial and Anti-Inflammatory Activity Against Periodontal Disease Treatment The rodent (rats and mice) ligature model of periodontitis is used. One day post ligature placement immediately following anesthesia, 50 µl of peptide or vehicle gel is topically applied on the gum area surrounding ligature. Animals are monitored until they recover consciousness. Gel is applied daily until animals are euthanized at the designated time points. Five animals from each group are euthanized after 7, 15, and 30 days post initiation of treatment. The maxillary jaws are hemisected and the gingival tissues are excised for assessment of tissue infection, inflammation and homogenate preparation for comparative cytokine analysis. Prior to processing, harvested tissue is weighed and values are expressed per gram of tissue weight.

Animal Groups

Animals (mice or rats) are randomly divided into 10 groups with 5 animals included in each of control and experimental groups (total 50 mice per experiment). Control animals establish baseline values. Untreated control animals receive applications of vehicle gel with no peptide. Animals are euthanized at 7, 15 and 30 days. The groups are shown in Table 6.

TABLE 6

| Group | MIce |
|---|---|
| 1 | Control animals with no ligature treated |
| 2 | Control animals with no ligature untreated |
| 3 | Control animals with ligature treated |
| 4 | Control animals with ligature untreated |
| 5 | Animals with ligature and Pg infection treated |
| 6 | Animals with ligature and Pg infection untreated |
| 7 | Animals with ligature and Fn infection treated |
| 8 | Animals with ligature, and Fn infection untreated |
| 9 | Animals with ligature and Pg and Fn infection treated |
| 10 | Animals with ligature and Pg and Fn infection untreated |

Example 12

In Vivo Assessment of Gel Formulations: Wound Healing and Tissue Regeneration Treatment The mouse oral wound-healing model is used. Mice receive daily gel applications and time course photographs of the wound areas are taken for each animal for photographic documentation of the wound site healing. The rates of healing of these wounds are followed over a 7-day period. While the animals are under anesthesia wound size is documented daily with a digital camera and images analyzed using NIH image 1.60 software by tracing the wound margin with a fine resolution computer mouse and calculating pixel area. The extent of wound closure is determined by relating pixel counts to a circular filter paper of the same diameter as the original wound that serves as a reference on every image. The measurements are performed in duplicate and mean values of consecutive tracings are computed and are expressed as a percentage of closure from the original wound. Also, acceleration in wound healing is indicated by a decline in levels of inflammatory cytokines at wounded areas, specifically TNF-α and IL-1β.

Animal Groups

Healthy age-matched BALB/cJ mice are divided randomly into 8 groups for each time point, with 5 mice in each group (40 mice per occasion). Control mice establish baseline values. Untreated control mice receive applications of vehicle gel with no peptide. Animal groups are euthanized at days 3, 5 and 7 and tongues are harvested and processed for analysis. The groups are shown in Table 7.

TABLE 7

| Group | MIce |
|---|---|
| 1 | Control unwounded mice (Day 0) |
| 2 | Control wounded mice (Day 2) |
| 3 | Mice with 1 treatment euthanized on Day 3 |
| 4 | Control mice untreated euthanized on Day 3 |
| 5 | Mice with 3 treatments euthanized on Day 5 |
| 6 | Control mice untreated euthanized on Day 5 |
| 7 | Mice with 5 treatments euthanized on Day 7 |
| 8 | Control mice untreated euthanized on Day 7 |

The following references are cited herein.

1. Kong et al. *Antimicrob. Agents Chemother.* February 2016 vol. 60 no. 2 881-889
2. Borg-von Zepelin et al. (1998) *Mol. Microbiol.* 28, 543-554
3. Schild et al., *Eukaryot. Cell* 10, 98-109, 2011.
4. Meiller et al., *PLoS One* 4, e5039, 2009.
5. Bochenska et al., *Biol. Chem.* 396:1369-1375, 2015.
6. Ruissen et al., *Biol. Chem.* 384:183-190, 2013.
7. Driscoll et al. *Gene* 177:29-34, 1996.
8. Tsai et al., *Infect. Immun.* 64:5000-5007, 1996.
9. Situ et al., *Biochimica et Biophysica Acta (BBA)-General Subjects* 1475:377-382, 2000.

The present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and all such variations are considered within the scope and spirit of the present invention.

What is claimed is:

1. A synthetic peptide of SEQ ID NO: 2, of SEQ ID NO: 3, of SEQ ID NO: 4, of SEQ ID NO: 5, of SEQ ID NO: 7, of SEQ ID NO: 8, of SEQ ID NO: 9, of SEQ ID NO: 10, of SEQ ID NO: 11, or of SEQ ID NO: 12.

2. The synthetic peptide of claim 1, further comprising an agent to improve uptake of the synthetic peptide conjugated thereto.

3. The synthetic peptide of claim 2, wherein the agent is spermidine or a polymeric delivery agent.

4. A pharmaceutical formulation, comprising:
the synthetic peptide of claim 1 and a biocompatible gelling agent formulated as a bioadhesive hydrogel.

5. The pharmaceutical formulation of claim 4, further comprising at least one antifungal agent or at least one antibacterial agent or a combination thereof.

6. The pharmaceutical formulation of claim 4, wherein the gelling agent has a concentration of at least 4% wt/wt in the pharmaceutical formulation.

7. The pharmaceutical formulation of claim 4, wherein the bioadhesive hydrogel is coated onto a bandage, a wound dressing a tissue, teeth, or an oral appliance.

8. A method for treating an oral infection associated with *Candida albicans* in a subject in need thereof, comprising: administering topically one or more times a hydrogel comprising at least one of the synthetic peptides of claim 1 to the subject.

9. The method of claim 8, wherein the hydrogel further comprises one or more antifungal agents.

10. The method of claim 8, wherein the hydrogel is bioadhesive.

* * * * *